United States Patent
Klaiman et al.

(10) Patent No.: US 12,026,875 B2
(45) Date of Patent: Jul. 2, 2024

(54) MACHINE LEARNING USING DISTANCE-BASED SIMILARITY LABELS

(71) Applicant: HOFFMANN-LA ROCHE INC., Little Falls, NJ (US)

(72) Inventors: Eldad Klaiman, Starnberg (DE); Jacob Gildenblat, Holon (IL)

(73) Assignee: Hoffmann-La Roche, Inc., Little Falls, NJ (US)

(*) Notice: Subject to any disclaimer, the term of this patent is extended or adjusted under 35 U.S.C. 154(b) by 309 days.

(21) Appl. No.: 17/431,334

(22) PCT Filed: Mar. 26, 2020

(86) PCT No.: PCT/EP2020/058570
§ 371 (c)(1),
(2) Date: Aug. 16, 2021

(87) PCT Pub. No.: WO2020/193708
PCT Pub. Date: Oct. 1, 2020

(65) Prior Publication Data
US 2022/0139072 A1 May 5, 2022

(30) Foreign Application Priority Data
Mar. 28, 2019 (EP) .................................. 19165965

(51) Int. Cl.
*G06T 7/00* (2017.01)
*G06N 3/045* (2023.01)
(Continued)

(52) U.S. Cl.
CPC .......... *G06T 7/0012* (2013.01); *G06N 3/045* (2023.01); *G06V 10/454* (2022.01);
(Continued)

(58) Field of Classification Search
CPC ......... G06T 7/0012; G06T 2207/30024; G06T 2207/20081; G06T 2207/20084;
(Continued)

(56) References Cited

U.S. PATENT DOCUMENTS 10,937,162 B2 * 3/2021 Sarkar .................... A61B 5/00
2016/0098589 A1   4/2016 Brieu
(Continued)

FOREIGN PATENT DOCUMENTS

JP   2009123234 A   6/2009
WO  2018/017355 A1  1/2018

OTHER PUBLICATIONS

David: "Neural Image Compression for Gigapixel Histopathology Image Analysis", arxiv.org, Cornell University Library, 201 Olin Library Cornell Universityu Ithaca, Nov. 7, 2018 (Nov. 7, 2018), XP081047191, NY 14853 (Year: 2018).*
(Continued)

*Primary Examiner* — Ping Y Hsieh
(74) *Attorney, Agent, or Firm* — Harness, Dickey & Pierce, P.L.C.

(57) ABSTRACT

The method includes receiving a plurality of digital images each depicting a tissue sample; splitting each of the received images into a plurality of tiles; automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity; and training a machine learning module—MLM—using the labeled tile pairs as training data to generate a trained MLM, the trained MLM being configured for performing an image analysis of digital histopathology images.

19 Claims, 9 Drawing Sheets

(51) Int. Cl.
| | |
|---|---|
| *G06V 10/44* | (2022.01) |
| *G06V 10/74* | (2022.01) |
| *G06V 10/764* | (2022.01) |
| *G06V 10/774* | (2022.01) |
| *G06V 10/82* | (2022.01) |
| *G06V 20/69* | (2022.01) |
| *G16H 30/40* | (2018.01) |

(52) U.S. Cl.
CPC .......... *G06V 10/761* (2022.01); *G06V 10/764* (2022.01); *G06V 10/7747* (2022.01); *G06V 10/82* (2022.01); *G06V 20/695* (2022.01); *G06V 20/698* (2022.01); *G16H 30/40* (2018.01); *G06T 2207/30024* (2013.01); *G06V 2201/03* (2022.01)

(58) Field of Classification Search
CPC ...... G06N 3/045; G06N 3/084; G06V 10/454; G06V 10/761; G06V 10/764; G06V 10/7747; G06V 10/82; G06V 20/695; G06V 20/698; G06V 2201/03; G16H 30/40; G06F 18/22
See application file for complete search history.

(56) References Cited

U.S. PATENT DOCUMENTS

| | | | | |
|---|---|---|---|---|
| 2017/0105601 | A1* | 4/2017 | Pheiffer | G06T 17/10 |
| 2019/0156954 | A1* | 5/2019 | Madabhushi | G16B 40/10 |
| 2019/0213736 | A1* | 7/2019 | Varekamp | G06T 7/0012 |
| 2020/0372635 | A1* | 11/2020 | Veidman | G06T 7/194 |

OTHER PUBLICATIONS

J. Bromley et al. 'Signature Verification using a 'Siamese' Time Delay Neural Network', AT&T Bell Laboratories, 1994, pp. 737-744.

R. Hadsell et al. 'Dimensionality Reduction by Learning an Invariant Mapping', The Courant Institute of Mathematical Sciences, 2006, pp. 1-8.

K. He et al. 'Deep Residual Learning for Image Recognition', 2015, pp. 1-12.

Z. Wu et al. 'Unsupervised Feature Learning via Non-Parametric Instance Discrimination', 2018, pp. 1-10.

International Search Report PCT/ISA/210 and Written Opinion of the International Searching Authority PCT/ISA/237 for International Application No. PCT/EP2020/058570 dated May 28, 2020.

David Tellez et al., "Neural Image Compression for Gigapixel Histopathology Image Analysis", arxiv.org, Cornell University Library, 201 Olin Library Cornell University Ithaca, Nov. 7, 2018 (Nov. 7, 2018).

Wouter M Kouw et al., "Learning an MR acquisition-invariant representation using Siamese neural networks", arxiv.org, Cornell University Library, 201 Olin Library Cornell University Ithaca, Oct. 17, 2018 (Oct. 17, 2018).

Ma Zongqing et al., "A discriminative learning based approach for automated nasopharyngeal carcinoma segmentation leveraging multi-modality similarity metric learning", 2018 IEEE 15th International Symposium on Biomedical Imaging (ISBI 2018), Apr. 4, 2018 (Apr. 4, 2018), p. 813-816.

International Preliminary Report on Patentability and Written Opinion dated Oct. 7, 2021 in International Application No. PCT/EP2020/058570.

European Office Action, dated Sep. 7, 2023, issued in corresponding European Patent Application No. 20713644.1.

Japanese Office Action, dated Feb. 6, 2024, issued in Japanese Patent Application No. 2021-552551.

Fukuma, Tomoki, et al., "Detecting Unlabeled Class by Intentional Clustering using Disentangled Representation." IEICE Technical Report, vol. 118, No. 284 [online], Oct. 29, 2018, Japan, The Institute of Electronics, Information and Communication Engineers, pp. 307-312.

\* cited by examiner

Fig. 11

MACHINE LEARNING USING DISTANCE-BASED SIMILARITY LABELS

CROSS-REFERENCE TO RELATED APPLICATIONS

This application is a national phase under 35 U.S.C. § 371 of PCT International Application No. PCT/EP2020/058570 which has an International filing date of Mar. 26, 2020, which claims priority to European Patent Application No. 19165965.5, filed Mar. 28, 2019, the entire contents of each of which are hereby incorporated by reference.

FIELD OF THE INVENTION

The invention relates to the field of digital pathology, and more particular to the field of image analysis.

BACKGROUND AND RELATED ART

The computational analysis of digital tissue images in the field of digital pathology has a wide range of important biomedical applications, e.g. tissue detection, segmentation, morphometry, identifying and classifying diseases, e.g. cancer, and potential treatment options. Currently, machine learning approaches are used in order to address the complexity and variety of the image analysis problems.

Typically, supervised machine learning approaches are used in order to an image analysis problem. Thereby, a machine learning module (MLM) is trained on a set of training images labelled as ground truth by domain experts (in particular pathologists and clinicians). During the training phase, the statistical model of the MLM learns to map relevant image features computed by an image analysis algorithm to the labels contained in the training data set.

These labels, also referred to as "annotations", may comprise metadata of the depicted tissue and/or of the patient from whom the tissue is derived. For example, the labels can indicate whether a tissue sample depicted in an image represents tumor tissue or healthy tissue, or whether the patient from which the depicted sample was taken responded to a particular drug. The label may indicate a particular tissue type or sub-type, e.g. if the tumor tissue is derived from a primary tumor or from a micro- or macro-metastase, from stroma tissue, muscle tissue, fat tissue, a background section of the slide or the like. The annotated training data set can be used for training a machine learning module (MLM) such that the MLM learns to automatically identify/predict the label based on a tissue pattern depicted in a new, unknown digital tissue image.

In digital pathology, annotated training data that is suited as a basis for supervised learning is scarce, because it is expensive and difficult to collect and annotate. Typically, training data is manually created by one or more domain experts who inspect and annotate a large number of digital tissue images. This costs a lot of time. The problem is of particular importance in the field of digital pathology, because the morphology of a tissue may strongly depend on many factors. For example, the morphology of lung cancer tissue, breast cancer tissue and liver cancer tissue may be different from each other. Hence, in order to generate a MLM that is able to predict a particular label, it may be necessary to create a training data set for each of the different cancer types. In fact, there exist many different sub-types of each of the above-mentioned cancer types. In order to correctly address the variety of different cancer-subtypes and other types of diseases, it would be desirable to provide a labeled training data set for each of the said diseases and disease sub-forms. However, as the annotation of such training data sets is time consuming and expensive, many biomedical questions cannot be addressed by currently available digital pathology methods due to a lack of annotated training data.

The problem is further exacerbated by the fact that in the context of training an MLM to solve a digital pathology problem, the identification of predictive features is an important but difficult task. Traditional handcrafted features rely heavily on the knowledge of domain experts. Often it is difficult or impossible even for domain experts to explicitly define a feature that can clearly be identified, that can be used for annotating an image data set and that is in addition predictive for the label of interest.

A further problem is associated with the fact that the assignment of labels such as a particular tissue type is sometimes subjective. When a training data set is annotated by many different pathologists, the labels may be inconsistent to a certain degree. As a consequence, the prediction accuracy of a MLM trained on this inconsistent training data set may be reduced because of a significant portion of "annotation inconsistency/annotation noise".

For the reasons described above, the scarcity of an annotated training data set of sufficient size and quality is currently the main reason why many open biomedical questions cannot be addressed and solved by the machine learning algorithm already available today.

SUMMARY

It is an objective of the present invention to provide for an improved computer-implemented learning method for digital pathology and a corresponding storage medium and image analysis system as specified in the independent claims. Embodiments of the invention are given in the dependent claims. Embodiments of the present invention can be freely combined with each other if they are not mutually exclusive.

In one aspect, the invention relates to a computer-implemented self-supervised learning method for digital pathology. The method comprises receiving a plurality of digital images, wherein each received image depicts a tissue sample; splitting each of the received images into a plurality of tiles; automatically generating tile pairs, wherein each tile pair has assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity; training a machine learning module (MLM) using the labeled tile pairs as training data to generate a trained MLM. The trained MLM is adapted for performing an image analysis of digital histopathology images.

This approach may be beneficial for multiple reasons: spatial proximity of two image regions is a feature that is always and inherently available in every digital image of a tissue sample. The problem is that spatial proximity of image and respective tissue regions per se typically do not reveal any relevant information in respect to a biomedical problem such as tissue type classification, disease classification, the prediction of the durability of a particular disease or an image segmentation task. Applicant has surprisingly observed that the information conveyed in the spatial proximity of two image regions ("tiles") is an accurate indicator of the similarity of the two image regions, at least if a large number of tiles and their respective distances is analyzed during the training phase of an MLM. Hence, by making use of the inherently available information "spatial proximity" of two tiles for automatically assigning a tissue pattern similarity label to the two compared tiles, a large annotated data set can be provided automatically that can be used for training a MLM. The trained MLM can be used for automatically determining if two images or image tiles received as input depict a similar or dissimilar tissue pattern. However, the data set can in addition be used for other and more complex tasks such as image similarity search, image segmentation, tissue type detection and tissue pattern clustering. Hence, applicant has surprisingly observed that the information conveyed in the spatial proximity of tiles can be used for automatically creating annotated training data that allows training an MLM that reliably determines the similarity of images and in addition may allow training an MLM that outputs a feature vector that can be used by additional data processing units for a plurality of complex image analysis tasks in digital pathology. None of these approaches requires a domain expert to annotate training data manually.

When an image of a tissue sample comprising many different tissue patterns (e.g. "non-tumor" and "tumor") is split into many different tiles, the smaller the distance between two tiles, the higher the probability that both compared tiles depict the same tissue pattern, e.g. "non-tumor". There will, however, be some tile pairs next to the border of two different patterns that depict different tissue pattern (e.g. the first tile "tumor", the other tile "non-tumor"). These tile pairs generate noise, because they depict different tissue patterns although they lie in close spatial proximity to each other. Applicant has surprisingly observed that this noise that is created by tile pairs spanning the border between different tissue patterns in combination with the simplifying assumption that spatial proximity indicates similarity of depicted tissue patterns does not reduce the accuracy of the trained MLM significantly. In fact, applicant observed that the accuracy of an MLM that was trained according to embodiments of the invention are able to outperform existing benchmark methods.

In a further beneficial aspect, it is now possible to quickly and fully automatically create training data for many different sets of images. Currently, there is a lack of available annotated datasets that capture the natural and practical variability in histopathology images. For example, even existing large datasets like Camelyon consist of only one type of staining (Hematoxylin and Eosin) and one type of cancer (Breast Cancer). Histopathology image texture and object shapes may vary highly in images from different cancer types, different tissue staining types and different tissue types. Additionally, histopathology images contain many different texture and object types with different domain specific meanings (e.g. stroma, tumor infiltrating lymphocytes, blood vessels, fat, healthy tissue, necrosis, etc.). Hence, embodiments of the invention may allow automatically creating an annotated data set for each of a plurality of different cancer types, cancer-sub-types, staining methods and patient groups (e.g. treated/non-treated, male/female, older/younger than a threshold age, biomarker-positive/biomarker-negative, etc.). Hence, embodiments of the invention may allow automatically creating annotated training data and training a respective MLM on the training data such that the resulting trained MLM is adapted to accurately address biomedical problems for each of a plurality of different groups of patients in a highly specific manner. Contrary to state of the art approaches where a MLM trained on a manually annotated breast cancer data set provided suboptimal results for colon cancer patients, embodiments of the invention may allow creating a MLM for each of the different patient groups separately.

According to embodiments, the label being indicative of the degree of similarity of two tissue patterns is a binary data value, i.e., a value that may have one out of two possible options. For example, the label can be "1" or "similar" and indicate that the two tiles depict a similar tissue pattern. Alternatively, the label can be "0" or "dissimilar" and indicate that the two tiles depict dissimilar tissue patterns.

According to other embodiments, the label can be more fine grained, e.g. can be a data value selected from a limited set of three or more data values, e.g. "dissimilar", "similar" and "highly similar".

According to still other embodiments, the label can be even more fine grained and can be a numerical value, wherein the amount of the numerical value positively correlates with the degree of similarity. For example, the numerical value can be computed as a function that linearly and inversely transforms the spatial distance between the two tiles in the pair into the numerical value representing tissue pattern similarity. The larger the spatial distance, the smaller the numerical value indicating tissue pattern similarity.

A large variety of MLM architectures exist which can process and use different types of labels in the training data set (e.g. ordinal or numerical values). The type of MLM is chosen such that it is able to process the automatically created labels of the training data set.

According to embodiments, the MLM is adapted to learn according to a supervised learning algorithm. Supervised learning is about finding a mapping that transforms a set of input features into one or more output data values. The output data values are provided during the training as labels, e.g. as a binary option label "similar" or "non-similar" or as a numerical value that is a quantitative measure for similarity. In other words, during the training, the data values that shall be predicted are explicitly provided to the model of the MLM in the form of the labels of the training data. Supervised learning comes with the problem that the training data needs to be labeled in order to define the output space for each sample.

According to embodiments, at least some or all of the tile pairs respectively depict two tissue regions contained in the same tissue slice. Each of the tissue slices is depicted in a respective one of the received digital images. The distance between tiles is computed within a 2D coordinate system defined by the x- and y-dimension of the received digital image from which the tiles in the pair have been derived.

According to embodiments, the tile pairs are generated by randomly selecting tile pairs within each of the plurality of different images. The random based selection ensures that the spatial distance between the tiles in each pair will vary. A similarity label, e.g. in the form of a numerical value that correlates inversely with the distance between the two tiles, is computed and assigned to each pair.

According to other embodiments, the tile pairs are generated by selecting at least some or all of the tiles of each received image as a starting tile; for each starting tile, selecting all or a predefined number of "nearby tiles", wherein a "nearby tile" is a tile within a first circle centered around the starting tile, whereby the radius of this circle is identical to a first spatial proximity threshold; for each starting tile, selecting all or a predefined number of "distant tiles", wherein a "distant tile" is a tile outside of a second circle centered around the starting tile, whereby the radius of the said circle is identical to a second spatial proximity threshold; the selection of the predefined number can be performed by randomly choosing this number of tiles within the respective image area. The first and second proximity threshold may be identical, but preferably, the second proximity threshold is larger than the first proximity threshold. For example, the first proximity threshold can be 1 mm and the second proximity threshold can be 10 mm. Then, a first set of tile pairs is selected, whereby each tile pair comprises the start tile and a nearby tile located within the first circle. Each tile pair in the first set is assigned the label "similar" tissue patterns. In addition, a second set of tile pairs is selected, whereby each pair in the said set comprises the start tile and one of the "distant tiles". Each tile pair in the second set is assigned the label "dissimilar" tissue patterns. For example, this embodiment may be used for creating "binary" labels "similar" or "dissimilar".

According to embodiments, the tissue sample comprises one or more tissue slices. For example, the tissue sample can be a tissue slice fixed to the surface of a slide, e.g. a glass slide. According to other examples, the tissue sample can be a tissue sample fixed to the surface of a slide, whereby the thickness (height, z-dimension) of the tissue sample allows obtaining multiple images for each of multiple layers in the z-dimension, each image corresponding to and depicting a tissue slide.

According to embodiments, the tiles of the plurality of tiles are non-overlapping tiles.

According to embodiments, the tile pairs comprise tile pairs of neighboring tiles and tile pairs of distant tiles.

According to embodiments, the tissue sample is an IHC tissue sample, i.e., a tissue sample having been stained with one or more Immunohistochemistry (IHC) staining methods. IHC typically involves the process of selectively identifying antigens (proteins) in cells of a tissue section by exploiting the principle of antibodies binding specifically to antigens in biological tissues. Immunohistochemical staining is used in the diagnosis of abnormal cells such as those found in cancerous tumors. Specific molecular markers are characteristic of particular cellular events such as proliferation or cell death (apoptosis). Immunohistochemistry is also used in basic research to understand the distribution and localization of biomarkers and differentially expressed proteins in different parts of a biological tissue.

For example, the tissue sample depicted in each of the images can be a tissue slice on a tissue slide, e.g. a glass slide.

According to embodiments, the distance between tiles is measured within the 2D coordinate system defined by the x and y axes of the digital image from which the tiles are derived. These embodiments may be used in a situation where a plurality of tissue sample images are available which depict tissue samples of different patients and/or of different regions within the same patient, whereby said different regions lie far away from each other or whereby the exact position of the said two regions relative to each other is unknown. In this case, the spatial proximity between tiles is measured only within the 2D plane of pixels defined by the digital image. Based on a known resolution factor of the image acquisition device (e.g. a camera of a microscope or a slide scanner), the distance between tiles of the original image can be used for computing the distance between the tissue regions in the tissue sample depicted by the two tiles.

According to embodiments, at least some or all of the tile pairs depict two tissue regions contained in two different tissue slices of a stack of adjacent tissue slices. Each of the tissue slices is depicted in a respective one of the received digital images. The received images depicting tissue slices of a stack of adjacent tissue slices are aligned with each other in a 3D coordinate system. The distance between tiles is computed within the 3D coordinate system.

For example, a subset of or all received digital images may depict tissue samples which are slices within a tissue block of adjacent tissue slices. In this case, the digital images can be aligned with each other in a common 3D coordinate system such that the position of the digital image in the 3D coordinate system reproduces the position of the respectively depicted tissue slices within the tissue block. This may allow determining the tile distance in a 3D coordinate system. The selection of "nearby" and "distant" tiles can be performed as described above for the 2D coordinate system case, with the only difference that the tiles in at least some of the tile pairs are derived from different ones of the received images.

According to some embodiments, the annotated training data comprises both tile pairs derived from the same digital image as well as tile pairs derived from different images having been aligned with each other in a common 3D coordinate system. This may be beneficial as the consideration of the third dimension (spatial proximity of tiles representing tissue regions in different tissue samples) may tremendously increase the number of tiles in the training data in case only a small number of images of respective tissue samples is available whereby the tissue samples belong to the same cell block, e.g. a 3D biopsy cell block.

According to embodiments, at least a further subset of the tile pairs comprises tile pairs depicting two tissue regions of the same tissue slice, wherein the distance (d1, d2) between the tiles of the tile pairs of the further subset is computed based on the same function of the spatial proximity as the distance between the tile pairs of the subset of tile pairs derived depicting different tissue slices. In other words, the function for computing the spatial proximity may use the same distance thresholds for two tiles in the 2D coordinate system of the same single tissue sample as for two tiles in the 3D coordinate system spanning two or more adjacent tissue slices.

According to embodiments, each tile depicts a tissue or background region having a maximum edge length of less than 0.5 mm, preferably less than 0.3 mm.

A small tile size may have the advantage that the number and area fraction of tiles depicting a mixture of different tissue patterns is reduced. This may help reducing the noise generated by tiles depicting two or more different tissue patterns and by tile pairs next to a "tissue pattern border" depicting two different tissue patterns. In addition, a small tile size may allow generating and labeling a larger number of tile pairs, thereby increasing the amount of labeled training data.

According to embodiments, the automatic generation of the tile pairs comprises: generating a first set of tile pairs using a first spatial proximity threshold; the two tissue regions depicted by the two tiles of each tile pair in the first set are separated from each other by a distance smaller than the first spatial proximity threshold; generating a second set of tile pairs using a second spatial proximity threshold; the two tissue regions depicted by the two tiles of each tile pair in the second set are separated from each other by a distance larger than the second spatial proximity threshold. For example, this can be implemented by selecting a plurality of start tiles, computing a first and a second circle based on the first and second spatial proximity threshold around each start tile and selecting tile pairs comprising the start tile and a "nearby tile" (first set) or a "distant tile (second set) as described already above for embodiments of the invention.

According to embodiments, the method comprises: selecting a start tile from the plurality of tiles; generating a first set of tile pairs using a first spatial proximity threshold, wherein the two tissue regions depicted by the two tiles of each tile pair in the first set are separated from each other by a distance smaller than the first spatial proximity threshold, and wherein each tile pair in the first set includes the start tile; generating a second set of tile pairs using a second spatial proximity threshold, wherein the two tissue regions depicted by the two tiles of each tile pair in the second set are separated from each other by a distance larger than the second spatial proximity threshold, and wherein each tile pair in the second set includes the start tile; selecting a different start tile from the plurality of tiles; and repeating the generating the first set of tile pairs, the generating the second set of tile pairs and the selecting the different start tile until each tile of the plurality of tiles has been selected as a start tile.

According to embodiments, the first and second spatial proximity thresholds are identical, e.g. 1 mm.

According to preferred embodiments, the second spatial proximity threshold is at least 2 mm larger than the first spatial proximity threshold. This may be advantageous, because in case the tissue pattern changes gradually from one into another pattern, the difference between the tissue pattern depicted in a "distant tile" compared to the tissue pattern depicted in a "nearby" tile may be clearer and the learning effect may be improved.

According to embodiments, the first spatial proximity threshold is a distance smaller than 2 mm, preferably smaller than 1.5 mm, in particular 1.0 mm.

In addition, or alternatively, the second spatial proximity threshold is a distance larger than 4 mm, preferably larger than 8 mm, in particular 10.0 mm.

These distance thresholds refer to the distance of the tissue regions (or slice background regions) depicted in the digital images and respective tiles. Based on a known magnification of the image acquisition device and the resolution of the digital image, this distance can be transformed in a distance within the 2D or 3D coordinate system of a digital image.

For example, the distance between tiles (and the tissue regions depicted therein) can be measured e.g. between the centers of two tiles in a 2d or 3D coordinate system. According to an alternative implementation variant, the distance is measured between the two tile edges (image region edges) lying closest to each other in the 2D or 3D coordinate system.

The above-mentioned thresholds have been observed to provide labeled training data that allows automatically generating a trained MLM that is accurately capable of identifying similar and dissimilar tissue patterns for breast cancer patients. In some other implementation examples, the first and second spatial proximity threshold may have other values. In particular in case a different set of received digital images showing different tissue types or cancer types is used, the first and second spatial proximity threshold may have other values than the above provided distance threshold values.

According to embodiments, the MLM is a Siamese neuronal network (or "Siamese network"). The Siamese network comprises two identical neuronal sub-networks joined by a common output layer. Each of the two neural sub-networks is adapted to extract a feature-vector from a respective one of the two tiles of a tile pair provided as input to the MLM. The output layer of the trained Siamese neuronal network is adapted to compute a label for each tile pair provided as input as a function of the two feature vectors. The label is indicative of a predicted similarity of the two tissue patterns depicted in the tile pair provided as input.

According to embodiments, the Siamese neuronal network is trained on the pairs of tiles using a loss function such that the similarity of the feature vectors extracted by the two sub-networks for the two tiles of the pair respectively correlates with the similarity of the tissue patterns depicted in the two tiles of the pair.

The Siamese network can be, for example, a Siamese network described in Bromley et al., "Signature Verification using a 'Siamese' Time Delay Neural Network, 1994, NIPS'1994. Each sub-network of the Siamese network is adapted to extract a multi-dimensional feature vector from a respective one of two image tiles provided as input. The network is trained on a plurality of tile pairs having been automatically annotated with proximity-based tissue-pattern-similarity labels with the objective that tile pairs depicting similar tissue patterns should have outputs (feature vectors) that are close (similar) to each other, and tile pairs depicting dissimilar tissue patterns should have outputs that are far from each other. According to one embodiment, this is achieved by performing a contrastive loss as described e.g. in Hadsell et al., Dimensionality Reduction by Learning an Invariant Mapping, 2006, CVPR'06. The contrastive loss is minimized during the training. The contrastive loss CL can be computed, for example, according to $$CL=(1-y)2(f1-f2)+y*\max(0, m-L2(f1-f2)),$$

wherein f1, f2 are the outputs two identical sub networks, and y is the ground truth label for the tile pair: 0 if they are labeled "similar" (first set of tile pairs), 1 if they are labeled "dissimilar" (second set of tile pairs).

As explained above, a straightforward way to generate pairs of similar and non-similar images in the field of digital pathology could be manually assigning annotations of different meaningful histopathological categories to the respective digital images or tiles. For example, if there are annotations of regions for different categories, it is possible to sample pairs of images inside the categories, and pairs of images between different categories. However generating this kind of a dataset diverse enough to capture the different types of categories is expensive and time consuming. Therefore, no appropriate training data is available for most of the relevant tissue types and patient groups. However, thanks to the automated annotation of digital tile pairs, the Siamese network can now be applied on a large number of different training data sets for addressing many different biomedical questions and problems.

According to embodiments, the MLM is a vector-output MLM. A "vector-output MLM" is a MLM that is adapted to receive a single digital image or a single tile and that is adapted to output a feature vector extracted from said tile, whereby the feature vector comprises features that are highly characteristic for this tissue pattern and that allow—based on a feature vector comparison with the feature vector extracted analogously from another image or tile to determine if the two compared images or tiles are similar. The features contained in each of the two feature vectors extracted from two different images or tiles are of high predictive relevance in respect to the question if the particular tissue patterns depicted in the said two images or tiles are similar or dissimilar.

Generating a vector-output-MLM on the automatically generated training data may be advantageous, because the output (a feature vector) generated by the trained vectoroutput-MLM allows addressing a large number of different problems and questions in digital pathology such as image segmentation, clustering, image similarity searches and the like. A trained Simian network that is trained on the automatically annotated training data expects to receive a pair of images or tiles and is adapted to automatically compute (predict) the similarity of the tissue patterns depicted in the two different tiles or images. However, some questions and problems in the field of digital pathology do not concern the similarity of two images but rather the similarity of a large number of images and/or do not concert tile similarity per se. Applicant has observed that the provision of a feature-vector MLM by training this MLM on an automatically labeled training data set is able to address also digital pathology problems like image segmentation and others, which may not directly correspond to the input and output data structures required/imposed by a Simian network architecture.

In machine learning and in image processing, feature extraction starts from an initial set of measured data and builds derived values (features) intended to be informative and non-redundant, facilitating the subsequent learning and generalization steps. During the training of an MLM, the MLM performs a dimensionality reduction process, where an initial set of raw features is reduced to a smaller and more manageable set of features for processing, while still accurately and completely describing the original data set. Preferably, a large number of features is derived from each tile, e.g. intensity gradient features, contrast features, features derived from the color channel, hue and/or saturation, and others. Existing image analysis tools and libraries may be employed for performing the feature extraction from the tiles. During the training of the MLM, the MLM according to embodiments o the invention transforms the set of originally extracted features into a reduced set of features (also named a feature vector). Determining a subset of the initial features is called feature selection. The selected features are expected to contain the relevant information from the input data, i.e., a single tile, so that the desired task (determination the similarity of the tissue pattern depicted in this tile in respect to a tissue pattern depicted in another tile) can be performed by using this reduced set of features represented in the output feature vector instead of the complete set of originally extracted features.

According to embodiments, the MLM comprises routines for extracting a plurality of features that are low level descriptors which give a description about color, shape, brightness, contrast, textures and other features that can be directly extracted from an image without the knowledge of a domain expert. In addition, or alternatively, the extracted features can comprise domain information descriptors giving information about objects and events in the respective biomedical domain. A concrete example would be objects having been automatically identified to be particular cell components, e.g. nuclei, cell membranes or other intracellular or extracellular structures, and/or cells of a particular type, e.g. "tumor cells", "stroma-cells", or cells expressing a particular biomarker of interest. Preferably, these domain information descriptors are identified in the received digital images fully automatically, so no manual inspection or annotation of the digital images is necessary.

According to embodiments, the MLM is or comprises a vector-output MLM. A vector-output MLM is a MLM that is adapted to receive a single digital image (or tile, i.e., a small image) as input and that is adapted to output a feature vector extracted from said image. The training of the MLM on the labeled tile pairs comprises a backpropagation operation. During backpropagation a predictive model of the MLM is changed such that the features in the vector extracted by the MLM comprises features that are characteristic for a particular tissue pattern and that enable a vector-comparison based identification of similar and dissimilar image pairs. In other words, during backpropagation, the parameters of the MLM are changed to create a feature vector for each input image that is able to correctly represent the image in a way that images that are similar have similar feature vectors and images that are dissimilar have dissimilar feature vectors. For example, the backpropagation can be based on a loss function that computes the loss in the form of the actual normalized distance between the two feature vectors (e.g. zero distance is label zero, i.e. similar and high distance is label one, i.e. dissimilar).

Creating a vector-output MLM by training it on the automatically labeled data set may be advantageous as the input/output structure of the vector-output-MLM may support a wide range of applications in the field of digital pathology, in particular vector based image similarity search, vector based clustering and image segmentation.

According to embodiments, the training of the vector-output MLM comprises: extracting, by the MLM, an initial feature vector from each of the tiles in the labeled tile pairs in the training data. The initially extracted features can be optical features such as brightness, contrast, color, gradient and other features. For example, a neural network pre-trained on the general image database ImageNet can be used for extracting a set of initial features from each input image. During backpropagation, the similarity labels and feature vectors of tiles of pairs are used for adapting the predictive model of the MLM such that the features in the output feature vector (which may only be a subset of the initially extracted features) represents the image in a way that images that are similar have similar feature vectors and images that are dissimilar have dissimilar feature vectors.

According to embodiments, the vector-output-MLM is a fully convolutional neural network comprising at least one bottleneck-layer.

According to one example, the vector-output-MLM has a UNET based network architecture. It has an input layer of with 512*512*3 (512×512 RGB) neurons and bottleneck layer with 9*9*128 neurons. Hence, the number of neurons in the bottleneck layer is about 1.5% of the number of neurons of the input layer.

According to another example, the network of the vector-output-MLM has a Resnet architecture that implements supervised or unsupervised learning algorithms. The input layer comprises 512×512×3 neurons and the bottleneck layer and the corresponding feature vector output by the bottleneck layer comprises typically 1024 or 2048 elements (neurons/numbers).

According to embodiments, the MLM is a Siamese network that comprises the vector-output-MLM in the form of one of its sub-networks. The method comprises providing of the vector-output-MLM by storing one of the sub-networks of the trained Siamese network separately on a storage medium and using the stored sub-network as the vector-output MLM.

This approach may be advantageous because it may not be necessary to perform an additional training of an additional MLM. Furthermore, it may not be necessary to become acquainted with the libraries and program frameworks required for implementing and training the vector-output-MLM in addition to the Siamese network. Rather, a single training phase is sufficient which returns as a result the trained Siamese network. The Siamese network can be used for all digital pathology problems where the similarity of tissue patterns depicted in a pair of images or in a pair of image tiles needs to be automatically be determined, because the Siamese network expects to receive a pair of images or tiles as input and returns a computed label being indicative of the similarity of the two depicted tissue patterns. The label can be a qualitative, binary label ("similar"/ "dissimilar") or a numerical value representing a quantitative degree of similarity. Then, by storing one of the sub-nets of the trained Siamese network separately and using this sub-network as the vector-output-MLM, the vector-output MLM can be used for addressing an even larger number of digital pathology problems, e.g. image similarity search problems where only a single search image or search tile is provided as input, or other tasks like image segmentation or tile based clustering problems. Hence, with a single training phase and based on a single MLM architecture, two different types of trained MLMs are provided which are adapted to receive different data structures as input and which are adapted to address different problems in the field of digital pathology.

According to embodiments, the computer-implemented method further comprises: providing a digital search image as input of the vector-output-MLM, the search image depicting a tissue sample or a sub-region thereof; extracting, by the vector-output-MLM, a search feature vector from the search image; performing, by a similarity search engine, a similarity search in an image database of digital tissue sample images, the similarity search engine determining the similarity of the search feature vector with feature vectors extracted by the vector-output-MLM for each of the images in the image database; and returning the ones of the images in the database whose feature vectors are the most similar to the search feature vector as a result of the similarity search.

According to embodiments, the similarity search engine extracts the feature vector from each of the images in the database dynamically during the similarity search. According to preferred embodiments, the feature vectors of the images in the database are pre-computed and stored in the database in association with the image from which they were extracted. This may have the advantage that the feature vector is computed only once and can then be re-used for many similarity searches. This may save CPU and memory capacity.

According to some embodiments, the images in the database are whole slide images and the search image is also a whole slide image or an image tile. According to other embodiments, the images in the database are image tiles and the search image is also an image tile.

This may be advantageous because a machine-learning based image similarity search is provided that encompasses domain-specific optical particularities of the images used for providing the training data set and that does not require any human intervention for creating the training data set.

According to embodiments, the computer-implemented method further comprises: providing a digital image as input of the vector-output-MLM, the digital image depicting a whole slide tissue sample or a sub-region thereof; splitting the provided digital image into a plurality of tiles; extracting, by the vector-output-MLM, a feature vector from each of the tiles; clustering, by a clustering engine, the feature vectors extracted from the plurality of tiles, thereby creating clusters of similar feature vectors; grouping the plurality of tiles into clusters of tiles in accordance with the clusters computed for the tiles' feature vectors; and outputting, via a graphical user interface, the clusters of tiles.

The grouping of tiles into clusters of tiles in accordance with the clusters computed for the tiles' feature vectors means that tiles whose feature vectors are similar are grouped into the same cluster.

This may be advantageous because a method for clustering image regions into clusters depicting similar tissue patterns is provided that encompasses domain-specific optical particularities of the images used for providing the training data set but nevertheless does not require any human domain expert to assign labels such as "tumor tissue", "slide background", "stroma tissue" to the respective tissue segment. It is also not necessary to specify in advance how many and what types of different tissue patterns are expected to be contained in a digital image. Rather, the clustering engine can identify similar tissue patterns and respective tiles fully automatically based on known clustering algorithms and the feature vectors computed by the self-supervised trained MLM.

For example, the clustering engine can use a k-means algorithm or hierarchical clustering algorithms for performing the vector-based clustering.

According to embodiments, the computer-implemented method further comprises: identifying segments in the provided digital image, wherein each segment is a group of adjacent tiles and wherein all tiles within each segment belong to the same one of the identified clusters of tiles; and outputting, via the graphical user interface, an optical indication of the identified segments in the provided digital image.

For example, the identified segments can be highlighted in the provided digital image with different colors or hatchlings. The identified image segments can be shown e.g. to the left or right of the original digital image or can be presented as semi-transparent overlay layer on top of the digital image. Hence, embodiments of the invention provide for an image segmentation method for digital pathology images that does not require a domain expert to manually identify and label tissue segment types of interest. Hence, a fully or largely automated, data-driven approach for image segmentation in the digital pathology domain is provided that is easily adaptable to any type of patient group or disease group for which a set of tissue images is available.

In a further aspect, the invention relates to a non-volatile storage medium comprising computer-interpretable instructions which, when executed by a processor, instantiate and/or execute a trained machine learning module— MLM—generated by a computer-implemented method according to any one of the embodiments and examples described herein.

In a further aspect, the invention relates to an image analysis system comprising at least one processor and a volatile or non-volatile storage medium. The storage medium comprises a trained a trained machine learning module—MLM—generated by a computer-implemented method according to any one of the embodiments and examples described herein.

The term "self-supervised learning" as used herein refers to a machine learning approach where the labels of a training data set are generated automatically. The architecture itself and the learning process can be entirely supervised but no manual annotation for creating the labeled training data is necessary.

The term "digital pathology" is an image-based information technology environment wherein computer technology is used for managing, extracting and processing information generated from a digital slide. Digital pathology is enabled in part by virtual microscopy, which is the practice of converting glass slides into digital slides that can be viewed, managed, shared and analyzed on a computer monitor.

A "tissue sample" as used herein is an assembly of cells that may be analyzed by the methods of the present invention. The assembly can be a slice of an in-vivo or ex-vivo cell block. For example, the tissue sample may be prepared from tissues collected from patients, e.g. a liver, lung, kidney or colon tissue sample from a cancer patient. The samples may be whole-tissue or TMA sections on microscope slides. Methods for preparing slide mounted tissue samples are well known in the art and suitable for use in the present invention.

Tissue samples may be stained using any reagent or biomarker label, such as dyes or stains, histochemicals, or immunohistochemicals that directly react with specific biomarkers or with various types of cells or cellular compartments. Not all stains/reagents are compatible. Therefore, the type of stains employed and their sequence of application should be well considered, but can be readily determined by one of skill in the art. Such histochemicals may be chromophores detectable by transmittance microscopy or fluorophores detectable by fluorescence microscopy. In general, cell containing samples may be incubated with a solution comprising at least one histochemical, which will directly react with or bind to chemical groups of the target. Some histochemicals are typically co-incubated with a mordant or metal to allow staining. A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes. Procedures for staining cell containing samples are well known in the art.

A "tissue pattern" as used herein is a regularity in a tissue sample (and hence, also a regularity in a digital image or tile depicting the region of the tissue sample comprising this tissue pattern. As such, the elements of a pattern repeat in a predictable manner or have some other characteristic visual features (e.g. a distinct color and/or brightness that allows discerning a particular tissue region comprising this pattern from another tissue region showing another pattern. Some tissue patterns may be directly observable and interpretable by a human domain experts. Other tissue patterns may be so complex that only a machine learning module is able to identify the pattern in an image. An image pattern may be characterized by a particular color, brightness, repetitive structures such as dots, lines, curves, spirals, meanders, waves, foams, tilings, cracks, and those created by symmetries of rotation and reflection.

An "image analysis system" as used herein is a system, e.g. a computer system, adapted to evaluate and process digital images, in particular images of tissue samples, in order to assist a user in evaluating or interpreting an image and/or in order to extract biomedical information that is implicitly or explicitly contained in the image. For example, the computer system can be a standard desktop computer system or a distributed computer system, e.g. a cloud system. Generally, computerized histopathology image analysis takes as its input a single- or multi-channel image captured by a camera and attempts to provide additional quantitative information to aid in the diagnosis or treatment.

A "digital image" as used herein is a numeric representation, normally binary, of a two-dimensional image. Typically, tissue images are raster type images meaning that the image is a raster ("matrix") of pixels respectively having assigned at least one intensity value. Some multi-channel images may have pixels with one intensity value per color channel. The digital image contains a fixed number of rows and columns of pixels. Pixels are the smallest individual element in an image, holding antiquated values that represent the brightness of a given color at any specific point. Typically, the pixels are stored in computer memory as a raster image or raster map, a two-dimensional array of small integers. These values are often transmitted or stored in a compressed form. A digital image can be acquired e.g. by digital cameras, scanners, coordinate-measuring machines, microscopes, slide-scanning devices and others.

A "label" as used herein is a data value, e.g. a string or a numerical value, that is assigned to a data record, e.g. a pair of tiles, and indicates a property associated with this tile pair. In particular, the label can be indicative of the similarity or dissimilarity of the two tiles in the tile pair having assigned the label.

An "image tile" as used herein is a sub-region of a digital image. In general, the tiles created from a digital image can have any shape, e.g. circular, elliptic, polygonal, rectangle, square or the like and can be overlapping or non-overlapping. According to preferred embodiments, the tiles generated from an image are rectangular, preferably non-overlapping tiles.

A "feature vector" as used herein is a data structure that contains information describing an object's important characteristics. The data structure can be a monodimensional or polydimensional data structure where particular types of data values are stored in respective positions within the data structure. For example, the data structure can be a vector, an array, a matrix or the like. The feature vector can be considered as an n-dimensional vector of numerical features that represent some object. In image analysis, features can take many forms. A simple feature representation of an image is the raw intensity value of each pixel. However, more complicated feature representations are also possible. For example, a feature extracted from an image or image tile can also be a SIFT descriptor feature (scale invariant feature transform). These features capture the prevalence of different line orientations. Other features may indicate the contrast, gradient orientation, color composition and other aspects of an image or image tile, or may be descriptive of the presence and/or distribution of more complex, domain specific objects such as nuclei, membranes, and/or one or more biomarkers of interest.

A "biomarker specific stain" as used herein is a stain that selectively stains a particular biomarker, e.g. a particular protein like HER, but not other biomarkers or tissue components in general.

A "non-biomarker specific stain" as used herein is a stain that has a more generic binding behavior. A non-biomarker specific stain does not selectively stain an individual protein or DNA sequence, but rather stains to a larger group of substances and sub-cellular as well as supra-cellular structures having a particular physical or chemical property. For example, Hematoxylin and eosin respectively are non-biomarker-specific stains. Hematoxylin is a dark blue or violet stain that is basic/positive. It binds to basophilic substances (such as DNA and RNA, which are acidic and negatively charged). DNA/RNA in the nucleus, and RNA in ribosomes in the rough endoplasmic reticulum are both acidic because the phosphate backbones of nucleic acids are negatively charged. These backbones form salts with basic dyes containing positive charges. Therefore, dyes like hematoxylin bind to DNA and RNA and stain them violet. Eosin is a red or pink stain that is acidic and negative. It binds to acidophilic substances such as positively charged amino-acid side chains (e.g. lysine, arginine). Most proteins in the cytoplasm of some cells are basic because they are positively charged due to the arginine and lysine amino-acid residues. These form salts with acid dyes containing negative charges, like eosin. Therefore, eosin binds to these amino acids/proteins and stains them pink. This includes cytoplasmic filaments in muscle cells, intracellular membranes, and extracellular fibers.

The term "intensity information" or "pixel intensity" as used herein is a measure of the amount of electromagnetic radiation ("light") captured on or represented by a pixel of a digital image. The term "intensity information" as used herein may comprise additional, related information, e.g. the intensity of a particular color channel. A MLM may use this information for computationally extracting derivative information such as gradients or textures contained in a digital image, and the derivative information may be implicitly or explicitly extracted from the digital image during training and/or during feature extraction by the trained MLM. For example, the expression "the pixel intensity values of a digital image correlate with the strength of one or more particular stains" can imply that the intensity information, including color information, allows the MLM and may also allow a user to identify regions in tissue sample having been stained with a particular one of said one or more stains. For example, pixels depicting a region of a sample stained with hematoxylin may have high pixel intensities in the blue channel, pixels depicting a region of a sample stained with fastRed may have high pixel intensities in the red channel.

A "machine learning module (MLM)" as used herein is a program logic, e.g. a piece of software like a neuronal network or a support vector machine or the like that has been or that can be trained in a training process and that—as a result of the learning phase—has learned to perform some predictive and/or data processing tasks based on the provided training data. Thus, an MLM can be a program code that is at least partially not explicitly specified by a programmer, but that is implicitly learned and modified in a data-driven learning process that builds one or more implicit or explicit models from sample inputs. Machine learning may employ supervised or unsupervised learning. Effective machine learning is often difficult because finding patterns is hard and often not enough training data are available. The MLM can be, for example, a stand-alone application program or a sub-module of an application program. It can be a locally installed program and/or can be implemented as a service provided to a plurality of clients via a network.

The term "biomarker" as used herein is a molecule that may be measured in a biological sample as an indicator of tissue type, normal or pathogenic processes or a response to a therapeutic intervention. In a particular embodiment, the biomarker is selected from the group consisting of: a protein, a peptide, a nucleic acid, a lipid and a carbohydrate. More particularly, the biomarker may be a particular protein, e.g. EGRF, HER2, p53, CD3, CD8, Ki67 and the like. Certain markers are characteristic of particular cells, while other markers have been identified as being associated with a particular disease or condition.

In order to determine the stage of a particular tumor based on an image analysis of a tissue sample image, it may be necessary to stain the sample with a plurality of biomarker-specific stains. Biomarker-specific staining of tissue samples typically involves the use of primary antibodies which selectively bind to the biomarker of interest. In particular these primary antibodies, but also other components of a staining protocol, may be expensive and thus may preclude the use of available image analysis techniques for cost reasons in many application scenarios, in particular high-throughput screenings.

Commonly, tissue samples are stained with a background stain ("counter stain"), e.g. a hematoxylin stain or a combination of hematoxylin and eosin stain ("H&E" stain) in order to reveal the large-scale tissue morphology and the boundaries of cells and nuclei. In addition to the background stain, a plurality of biomarker-specific stains may be applied in dependence on the biomedical question to be answered, e.g. the classification and staging of a tumor, the detection of the amount and relative distribution of certain cell types in a tissue or the like.

BRIEF DESCRIPTION OF THE DRAWINGS

In the following embodiments of the invention are explained in greater detail, by way of example only, making reference to the drawings in which:

FIG. 11 shows a similarity search result generated by a MLM trained on an automatically labeled data set.

FIG. 1 depicts a flowchart of a method 100 according to an embodiment of the invention. The method can be used e.g. for providing a trained MLM that is adapted to automatically determine the similarity of tissue patterns depicted in two input images. in addition, or alternatively, a trained MLM is provided that is adapted to extract a feature vector from an input image that is highly characteristic for the tissue pattern depicted in this image and that can be used as a basis for a bunch of applications in the domain of digital pathology such as similarity image search, similarity-based clustering of image regions and image segmentation.

Figure 1:
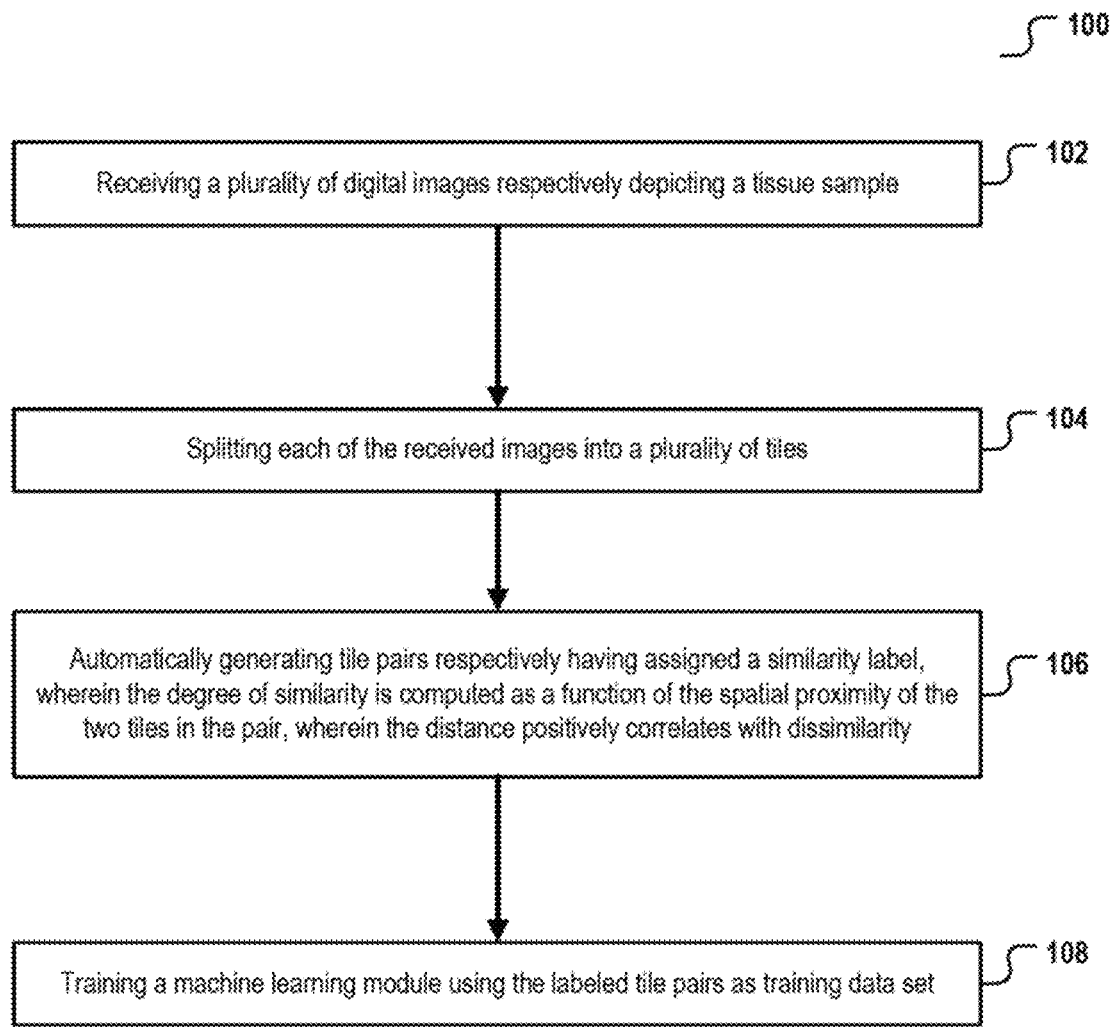
FIG. 1 depicts a flowchart of a method according to an embodiment of the invention.

The method 100 allows automatically creating an annotated training data set in a biomedical domain of interest that can be used as a basis for creating the above-mentioned MLM.

In a first step 102, an image analysis system receives a plurality of digital images respectively depicting a tissue sample of a patient. For example, the images can be received directly from an image capturing devices, e.g. from a camera of a brightfield microscope, a fluorescent microscope or a slide scanning device. In addition, or alternatively, the images can be read from a local or remote data storage device. The reading can comprise reading the images from a database. For example, the images can be tissue sample images being many years old. Old image datasets may have the advantage that the outcome of many relevant events, e.g. treatment success, disease progression, side effects are meanwhile known and can be used for creating a training data set comprising tissue images having assigned the known events as additional labels.

For each patient, one or more images can be received by the image analysis system. For example, the same tissue sample can be stained multiple times according to different staining protocols, whereby for each staining protocol an image is acquired. In addition, or alternatively, several adjacent tissue sample slices may respectively stained with the same or with different staining protocols and for each of the tissue sample slides an image is acquired. preferably, all received images depicts tissue samples having been stained according to the same staining protocol and having been derived from a cohort of patients sharing a relevant biomedical attribute, e.g. "breast cancer patients" or "colon cancer patients".

according to one example implementation, the digital tissue sample images published as a basis for the "CAMELYON16" challenge 2016 can be used as a basis for creating the automatically labeled training data set. The CAMELYON16 data set consists of 270 whole slide images of H&E stained lymph node tissue sections of breast cancer patients is provided as a training image data set (160 images of normal tissue, 110 images with tumor metastases). The data set is available under https://camelyon16.grand-challenge.org/data/.

Next in step 104, the image analysis system splits each received image into a set of image tiles. For example, in the case of the CAMELYON16 data set, at 10× magnification the images of this dataset can be used for generating 1,113,403 RGB tiles from non-background areas of size 256×256 pixels each with no overlap.

Next in step 106, the image analysis system automatically creates an annotated training data set. The creation of the annotated training data set comprises selecting a plurality of pairs of tiles and automatically assigning a label to each pair. The label is an indicator of the degree of similarity of the two tissue patterns depicted by the two tiles of the pair. The label is automatically computed as a function of the spatial distance of the two tiles of the pair (and hence, implicitly, as a function of the distance of the two tissue regions depicted by the two tiles of the pair). The label can be computed as a qualitative value, e.g. as a value that is either "similar" or "non-similar". Of course, these two options may likewise be represented by other strings or by a pair of numerical values such as "0" and "1". this step is based on the observation that the spatial proximity information that is inherently comprised in any digital image of a tissue slide can be used for automatically creating annotations in a training data set that is of significant predictive value for many problems and digital pathology that can be addressed by machine learning algorithms.

Next in step 108, a machine learning module is trained using the automatically labeled tile pairs as training data set. For example, and as described with reference to FIGS. 4, 5 and 9, the machine learning module can be a neural network, in particular a Siamese network. The trained Siamese network is adapted to receive a pair of images (or a pair of tiles, whereby a tile can be considered to be a small image) as input and automatically computed, based on the trained prediction model, a label indicating the degree of similarity of the tissue patterns depicted in the received pair of images.

In addition, or alternatively, a machine learning module (referred herein as vector-output-MLM) is trained using the automatically labeled tile pairs as training data set that is adapted to compute a feature vector from an individual image (or tile), whereby the feature vector is characteristic for the tissue pattern depicted in a tile and allows to compute the similarity/dissimilarity of images as a function of a comparison of the two feature vectors extracted by the respective images by the trained vector-output-MLM. Preferably, the vector-output-MLM is created as a truncated version of a trained Siamese network and can be used for a variety of different use case scenarios (see figure description of FIGS. 6, 7 and 8).

Figure 2A:
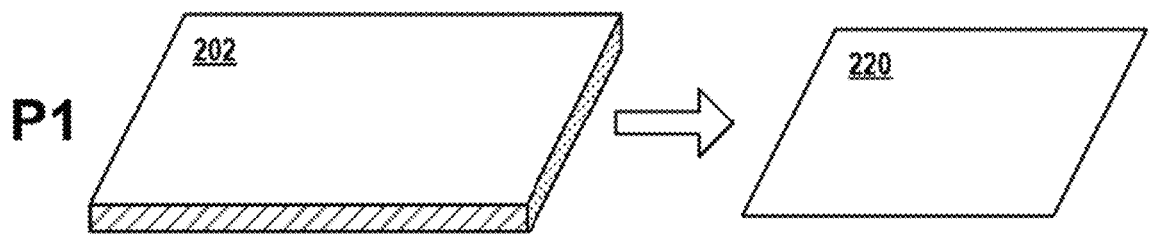
FIGS. 2A and 2B depict digital images depicting a respective tissue sample.
Figure 2A:
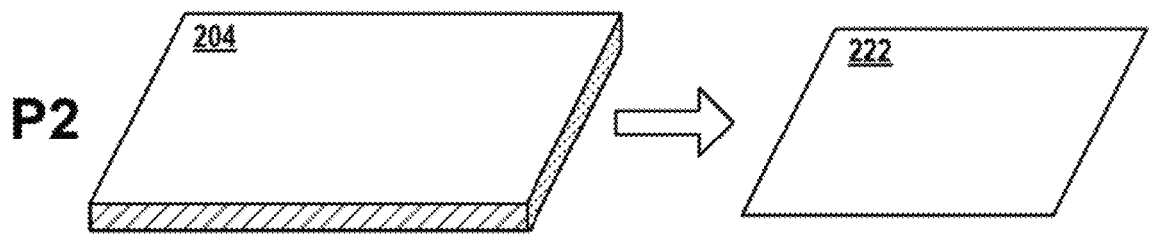
Figure 2A:
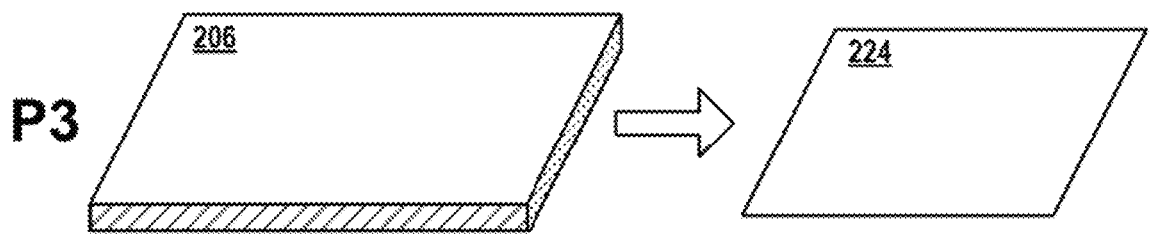

FIG. 2A depicts three digital images 220, 222, 224 respectively depicting a tissue sample 202, 204, 206 of three different patients P1, P2, P3. After the tissue samples are obtained from a patient, they are set on microscopy slides and are stained with one or more histologically relevant stains, e.g. H&E and/or various biomarker specific stains. Images are taken from the stained tissue samples using e.g. a slide scanner microscope. As the tissue samples are derived from different patients, it is not possible to align the digital images into a 3D coordinate system. In this case, the tile distance is computed within a 2D space defined by the x and y coordinate of an image. In the following, the determination of the tile distances is described for the digital images and tiles.

Figure 2B:
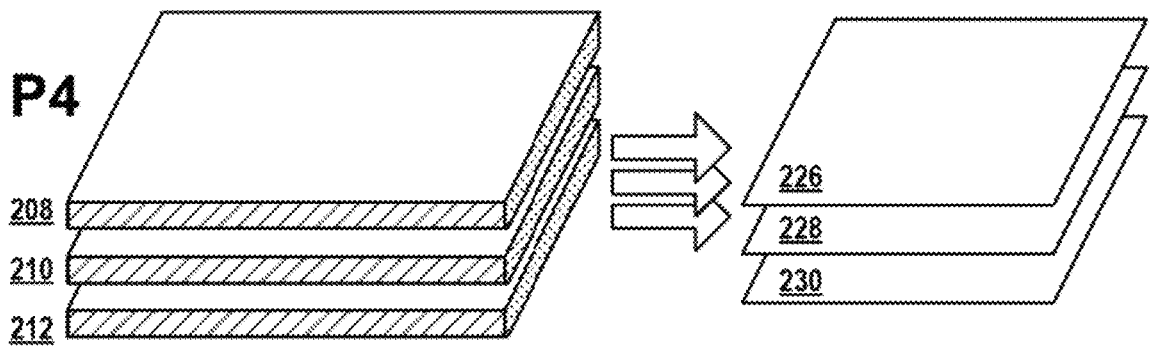
Figure 2B:
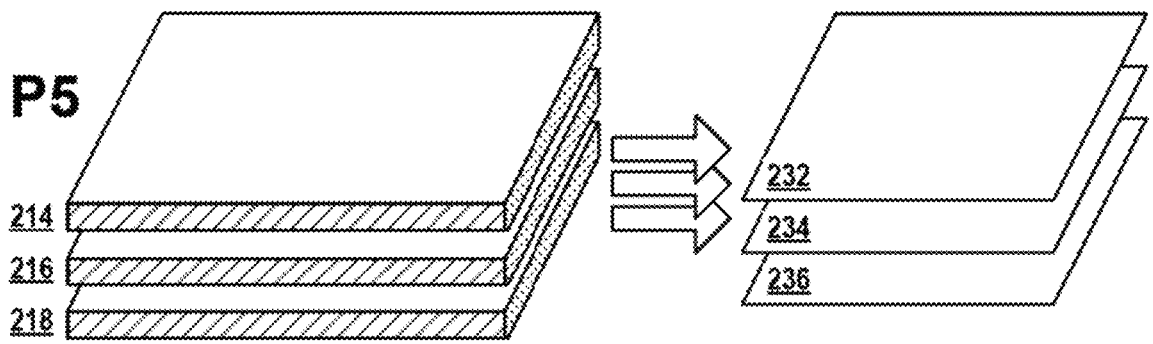

FIG. 2B depicts three digital images 226, 228, 230 respectively depicting a tissue sample 208, 210, 212 derived from a single tissue block of a particular patient P4. The depicted tissue samples belong to a stack of multiple adjacent tissue slices. For example, this stack of tissue slices can be prepared ex-vivo from a FFPET tissue block. The tissue blocks are sliced and the slices set on microscopy slides. Then, the slices are stained as described with reference to FIG. 2A.

As the tissue samples within this stack are derived from a single tissue block, it is possible to align the digital images 226, 228, 230 depicting the tissue slices 208, 210, 212 within a common 3D coordinate system, whereby the z-axis is orthogonal to the tissue slices. Analogously, the three digital images 232, 234 and 236 depicts three respective tissue samples 214, 216, 218 derived from another single tissue block of another patient P5. It is possible to align the digital images 232, 234 and 236 within a common 3D coordinate system, whereby the z-axis is orthogonal to the tissue slices.

In this case, the tile distance is computed within a 2D space in case the two tiles of a pair are derived from the same image. In addition, tile pairs can be created whose tiles are derived from different images aligned to each other in a common 3D coordinate system. In this case, the distance of the two tiles in a pair is computed using the 3D coordinate system.

Figure 3A:
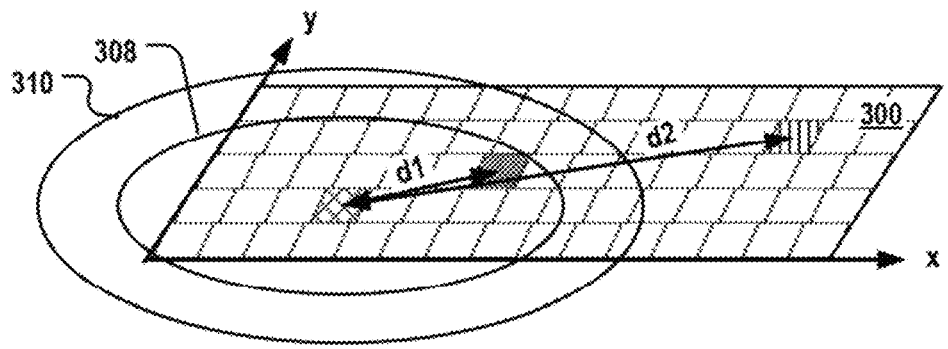
FIGS. 3A and 3B illustrate spatial distances of tiles in a 2D and a 3D coordinate system.
Figure 3A:
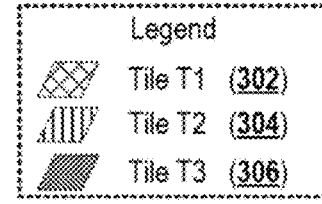

FIG. 3A illustrates spatial distances of tiles in a 2D coordinate system defined by the x and y axes of a digital tissue sample image 300. The digital image 300 has been split into a plurality of tiles. For illustration purposes, the size of the tiles in FIG. 3A is larger than the typical tile size.

A training data set can be labelled automatically by the following approach: at first, a start tile 302 is selected. Then, a first circular area around this start tile is determined. The radius of the first circle is also referred to as first spatial proximity threshold 308. All tiles within this first circle, e.g. tile 306, are considered to be a "nearby" tile of the start tile 302. In addition, a second circular area around this start tile is determined. The radius of the second circle is also referred to as second spatial proximity threshold 310. All tiles outside of this second circle, e.g. tile 304, are "distant" tiles in respect to the start tile 302.

Then, a first set of tile pairs is created, wherein each tile pair of the first set comprises the start tile and a "nearby" tile of the start tile. For example this step can comprise creating as many tile pairs as nearby tiles are contained in the first circus. Alternatively, this step can comprise randomly selecting a subset of available nearby tiles and creating a tile pair for each of the selected nearby tiles by adding the start tile to the selected nearby tile.

A second set of tile pairs is created. Each tile pair of the second set comprises the start tile and a "distant" tile in respect to the start tile. For example, this step can comprise creating as many tile pairs as distant tiles are contained in the image 300 outside of the second circle. Alternatively, this step can comprise randomly selecting a subset of the available distant tiles and creating a tile pair for each of the selected distant tiles by adding the start tile to the selected distant tile.

Then, another tile within image 300 can be used as starting tile and the above mentioned steps can be performed analogously. This means that the first and second circles are redrawn using the new start tile as the center. Thereby, nearby tiles and distant tiles in respect to the new start tile are identified. The first set of tiles is supplemented with pairs of nearby tiles identified based on the new start tile and the second set of tiles is supplemented with pairs of distant tiles identified based on the new start tile.

Then, still another tile within image 300 can be selected as a start tile and the above mentioned steps can be repeated, thereby further supplementing the first and second tile pair sets with further tile pairs. The selection of new start tiles can be performed until all tiles in the image have once been selected as start tile or until a predefined number of tiles has been selected as start tile.

To each of the tile pairs in the first set, e.g. pair 312, the label "similar" is assigned. To each of the tile pairs in the second set, e.g. pair 314, the label "dissimilar" is assigned.

Figure 3B:
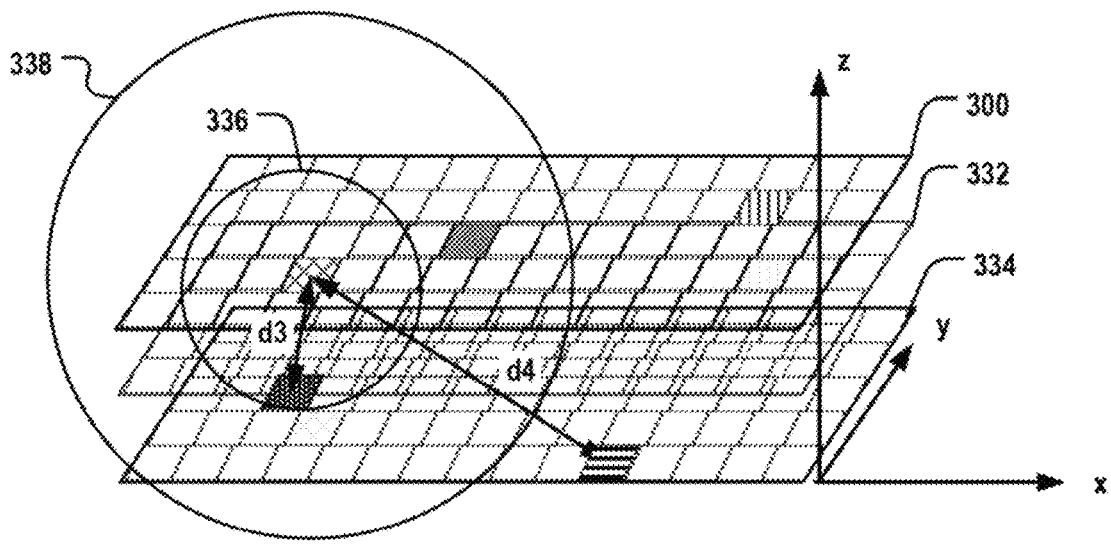
Figure 3B:
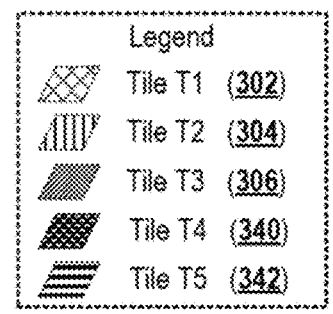

FIG. 3B illustrates spatial distances of tiles in a 3D coordinate system defined by the x and y axes of a digital tissue sample image 300 and a z axis corresponding to the height of a stack of images 300, 332, 334 aligned to each other in accordance with the relative position of a tissue block's tissue slices respectively depicted by the images 300, 332, 334. The distance of the images in z direction corresponds to the distance of the tissue slices depicted by the said images. Each of the aligned digital images has been split into a plurality of tiles. For illustration purposes, the size of the tiles in FIG. 3B is larger than the typical tile size.

A training data set can be labelled automatically by the following approach: at first, a start tile 302 is selected. Then, tile pairs comprising the start tile and a nearby tile and tile pairs comprising the start tile and a distant tile are identified and labeled as described below.

A first 3D sphere around this start tile is determined. For illustration purposes, only a cross-section of the first sphere is shown. The radius of the first sphere is also referred to as first spatial proximity threshold 336. All tiles within this first sphere, e.g. tile 306 in image 300, but also tile 340 in image 334, are considered to be a "nearby" tile of the start tile 302. In addition, a second sphere around this start tile is determined. The radius of the second sphere is also referred to as second spatial proximity threshold 338. All tiles outside of this second sphere, e.g. tile 304 of image 300, but also tile 342 of image 334, are "distant" tiles in respect to the start tile 302.

A first set of tile pairs is created, wherein each tile pair of the first set comprises the start tile and a "nearby" tile of the start tile. For example this step can comprise creating as many tile pairs as nearby tiles are contained in the first sphere. Alternatively, this step can comprise randomly selecting a subset of available nearby tiles and creating a tile pair for each of the selected nearby tiles by adding the start tile to the selected nearby tile.

A second set of tile pairs is created. Each tile pair of the second set comprises the start tile and a "distant" tile in respect to the start tile. For example, this step can comprise creating as many tile pairs as distant tiles are contained in the images 300, 332, 334 outside of the second sphere. Alternatively, this step can comprise randomly selecting a subset of the available distant tiles and creating a tile pair for each of the selected distant tiles by adding the start tile to the selected distant tile.

Then, another tile within image 300 or within image 332, 334 can be used as starting tile and the above mentioned steps can be performed analogously. This means that the first and second spheres are redrawn using the new start tile as the center. Thereby, nearby tiles and distant tiles in respect to the new start tile are identified. The first set of tiles is supplemented with pairs of nearby tiles identified based on the new start tile and the second set of tiles is supplemented with pairs of distant tiles identified based on the new start tile.

The above mentioned steps can be repeated until every tile in each of the received images 300, 332, 334 has been selected as start tile (or until another termination criterium is fulfilled), thereby further supplementing the first and second tile pair sets with further tile pairs.

To each of the tile pairs in the first set, e.g. pair 312 and 313, the label "similar" is assigned. To each of the tile pairs in the second set, e.g. pair 314 and 315, the label "dissimilar" is assigned.

The circle and sphere-based distance computation illustrated in FIGS. 3A and 3B are only examples for computing distance-based similarity labels, in this case binary labels being either "similar" or dissimilar". Other approaches can likely be used, e.g. computing the Euclidian distance between two tiles in a 2D or 3D coordinate system and computing a numerical similarity value that negatively correlates with the Euclidean distance of the two tiles.

As the number of pixels that correspond to one mm tissue depends on various factors such as magnification of the image capturing device and the resolution of the digital image, all distance thresholds will herein be specified with respect to the depicted real physical object, i.e., a tissue sample or a slide covered by a tissue sample.

Figure 4:
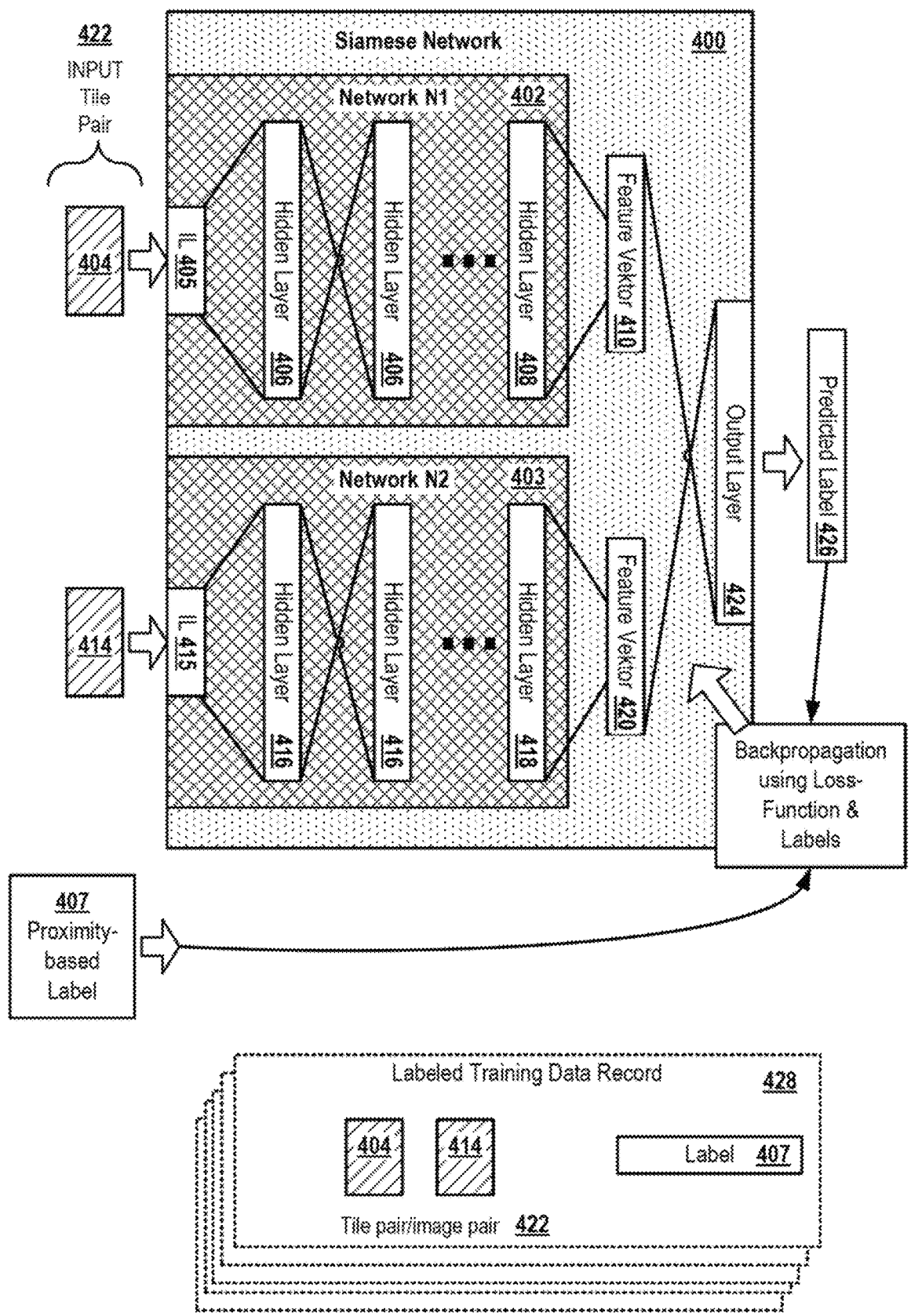
FIG. 4 depicts the architecture of a Siamese network according to an embodiment of the invention.

FIG. 4 depicts the architecture of a Siamese network 400 used as the MLM to be trained on the automatically labeled training data according to an embodiment of the invention.

The Siamese network 400 consists of two identical sub networks 402, 403 joined at their output layer 424. Each network comprises an input layer 405, 415 adapted to receive a single digital image (e.g. a tile) 404, 414 as input. Each sub-network comprises a plurality of hidden layers 406, 416, 408, 418. A one-dimensional feature vector 410, 420 is extracted from one of the two input images by a respective one of the two sub networks. Thereby, the last hidden layer 408, 418 of each network is adapted to compute the feature vector and provide the feature vector to the output layer 424. The processing of the input images is strictly separated. This means, that sub-network only processes the input image 404 and sub-network only processes the input image 414. The only point where the information conveyed in the two input images is combined is in the output layer when the output layer compares the two vectors for determining vector similarity and hence, the similarity of the tissue patterns depicted in the two input images.

According to embodiments, each sub-network 402, 403 is based on a modified res-net-50 architecture (He et al., Deep Residual Learning for Image Recognition, 2015, CVPR'15). According to embodiments, the resnet-50 pretrained sub-networks 402, 403 were pre-trained on ImageNet. The last layer (that normally outputs 1,000 features) is replaced with a fully connected layer 408, 418 of a size having the desired size of the feature vector, e.g. size 128. For example, the last layer 408, 418 of each sub-network can be configured to extract features from the second last layer, whereby the second last layer may provide a much greater number of features (e.g. 2048) than the last layer 408, 418. According to embodiments, an optimizer, e.g. the Adam optimizer with the default parameters in PyTorch (learning rate of 0.001 and betas of 0.9, 0.999), and a batch size of 256 was used during the training. For data augmentation, random horizontal and vertical flips and/or a random rotation up to 20 degrees, and/or a color jitter augmentation with a value of 0.075 for brightness, contrast saturation and/or hue can be applied on the tiles for increasing the training data set.

When the Siamese network is trained on pairs of automatically labeled images, it is the objective of the learning process that similar images should have outputs (feature vectors) that are similar to each other, and dissimilar images should have outputs that are dissimilar to each other. This can be achieved by minimizing a loss function, e.g. a function that measures the contrastive.

The training of the Siamese network 400 comprises feeding the network 400 with a plurality of automatically labeled similar 312, 313 and dissimilar 314, 315 tile pairs. Each input training data record 428 comprises the two tiles 404, 414 of the tile pair and its automatically assigned, spatial-proximity-based label 407. The proximity-based label 407 is provided as the "ground truth". The output layer 424 is adapted to compute a predicted similarity label for the two input images 404, 414 as a function of the similarity of the two compared feature vectors 408, 418. The training of the Siamese network comprises a back propagation process. Any deviation of the predicted label 426 from the input label 407 is considered to be an "error" or "loss" that is measured in the form of a loss function. The training of the Siamese network comprises minimizing the error computed by the loss function by iteratively using back propagation. The Siamese network 400 can be implemented, for example, as described by Bromley et al. in "Signature Verification using a "Siamese" Time Delay Neural Network", 1994, NIPS'1994.

Evaluation of MLM Prediction Accuracy

According to one example embodiments, the automatically labeled training data set was extracted from the Camelyon16 dataset at ×10 resolution. The Camelyon16 training dataset contains 270 breast lymph node Hematoxylin and Eosin (H&E) stained tissue whole slide images. At first, the images in the Camelyon16 data set were split into non overlapping tiles of size 224×224. A maximum distance of 1792 pixels between two tiles were used as first spatial proximity threshold, meaning that tile pairs having a distance smaller than 1792 pixels were automatically labeled "similar" tile pairs. A distance of 9408 pixels was used as second spatial proximity threshold, meaning that tile pairs having a distance of more than 9408 pixels were labeled as "dissimilar" tiles. Sampling 32 pairs of near tiles and 32 pairs of distant tiles yielded a dataset of 70 million pairs of which 35 million are labeled "similar", and 35 million are labeled "non similar". These automatically labeled tile pairs were used for training the Simian network 400. As a training loss on pairs of images, the contrastive loss was used. The Siamese network 400 was trained for 24 hours, by which time it had managed to iterate over 30 million image pairs, roughly equivalent to 40% of the image pairs in the training set. Training was done using 8 V100 GPUs on the Roche Pharma HPC using a PyTorch DataParallel implementation.

Then, the accuracy of the trained Siamese network was validated on the Camelyon16 testing set which contains 130 whole slide images of breast cancer tissue. The accuracy of the trained Siamese network is the ability of the learned network to separate between near and distant tiles, under the assumption that neighboring tiles look more similar than distant tiles. For every tile in the Camelyon16 test set, 8 near tiles and 8 distant tiles were used as a basis for sampling for data augmentation. The data augmentation was performed using random horizontal and vertical flips, random rotation up to 20 degrees, a color jitter augmentation with a value of 0.075 for brightness, contrast saturation and hue. This resulted in 1,385,288 pairs of neighboring tiles, and 1,385,288 distant tiles.

Then the Global Average Descriptor Distance Ratio (ADDR) is computed for the test tile pairs. The ADDR consists of the ratio between the average L2 distance between descriptors of all distant tile pairs ("non-similar" pairs), and the average L2 distance between descriptors of all neighboring tile pairs ("similar" pairs) in the augmented test data set. In addition, the median of the per tile ADDR is computed. The median of the per tile ADDR consists of a per tile calculation of the ratio between the average L2 distance between descriptors of all distant pairs this tile is a member of and the average L2 distance between descriptors of all neighboring pairs this tile is a member of. Results are given in the table below:

| L2 distance ratio between descriptors of distant and near tiles Method | Global ADDR | Median Per-Tile ADDR |
|---|---|---|
| Resnet-50 pretrained on ImageNet | 1.38 | 1.33 |
| Non-Parametric Instance Discrimination (Wu et al., Unsupervised Feature Learning via Non-Parametric Instance Discrimination, 2018, preprint arXiv:1805.01978) | 1.28 | 1.27 |
| Simian network 400 trained on an automatically labeled training data (proximity-based similarity) | 1.5 | 1.49 |

Based on the results from this experiment, it seems an MLM trained according to embodiments of the claimed invention outperforms the benchmark methods in the task of separating near and distant (or "similar" and "non-similar") tiles in descriptor space on the test set than the other examined benchmark methods.

Evaluation of MLM Based Tumor Tile Retrieval

Furthermore, it was observed that the method of training an MLM according to embodiments of the invention in addition can lead to better image retrieval performance. In a further experiment, the ability of the learned vector-output MLM 402, 403 to perform a pathology image retrieval task was evaluated. The vector-output MLM was obtained by separately storing one of the sub-networks of the trained Simian network 400 on a data storage unit and using the sub-network ("truncated Siamese network") as the trained MLM to be used in the image similarity search.

For every tile extracted from the Camelyon16 testing set, the supplied tumor metastases annotations were used to mark if they belong to a tumor region or not. If the tile is entirely inside a tumor region, the tile was labeled a "tumor" tile. 3809 tiles were marked as tumor tiles, consisting 3% of the total amount of tiles. Then for every tumor tile, a nearest neighbor search based on feature vectors output by the vector-output MLM 402, 403 was performed, constraining the search to tiles from other slides in order to more robustly assess descriptor generalization across different images. Examples for results from the retrieval task are presented in FIG. 11.

| Results for tumor tile retrieval Method | Ratio of retrieved tumor tiles |
|---|---|
| Resnet-50 pretrained on ImageNet | 26% |
| Non-Parametric Instance Discrimination (Wu et al., Unsupervised Feature Learning via Non-Parametric Instance Discrimination, 2018, preprint arXiv:1805.01978) | 21% |
| Method according to an embodiment of the invention | 34% |

The two tests reveal that a novel self-supervised approach for training an MLM for the purpose of generating visually meaningful image descriptors is provided that yields substantially better image retrieval results than other benchmark methods on the Camelyon16 dataset. The spatial-distance derived similarity labels have been demonstrated to provide highly meaningful and accurate descriptors for tissue pattern similarity and image retrieval. In addition, an improved feature extraction algorithm for digital pathology datasets is provided that can be applied also on digital pathology problems where labels for a supervised training are hard or impossible to obtain. The two tests revealed that the spatial-proximity based similarity labels provide meaningful descriptors of real tissue similarity (e.g. tumor/non-tumor).

Figure 5:
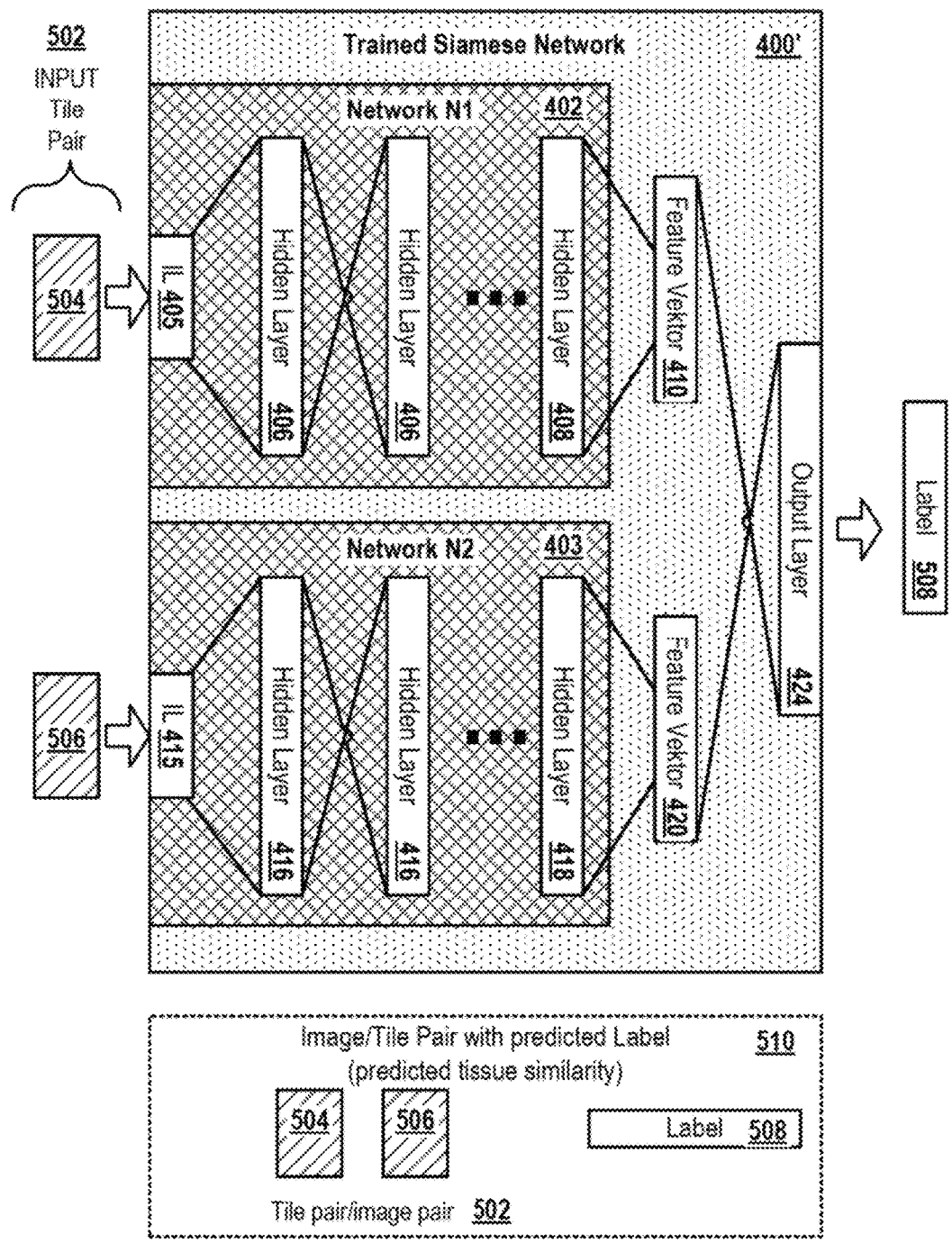
FIG. 5 depicts the use of a trained Siamese network according to an embodiment of the invention.

FIG. 5 depicts the trained version 400' of the Siamese network 400 shown in FIG. 4. The trained Siamese network 400' expects to receive a pair 502 of images (e.g. tiles) 504, 506 as input. The trained sub-networks 402, 403 of the trained network 400' is adapted to extract a feature vector from each of the input images, whereby the extracted features of the feature vectors are feature which are of particular predictive relevance in respect to the question if two compared digital tissue images are similar or not. The output layer 424 of the trained Siamese network compares the two feature vectors and predicts and outputs a similarity label 508 as a function of the two feature vectors extracted from the input images 504, 506. Hence, the trained Siamese network 400' is adapted to complete a data record 510 by computing a predicted similarity label 508 for an input pair 502 of images.

Figure 6:
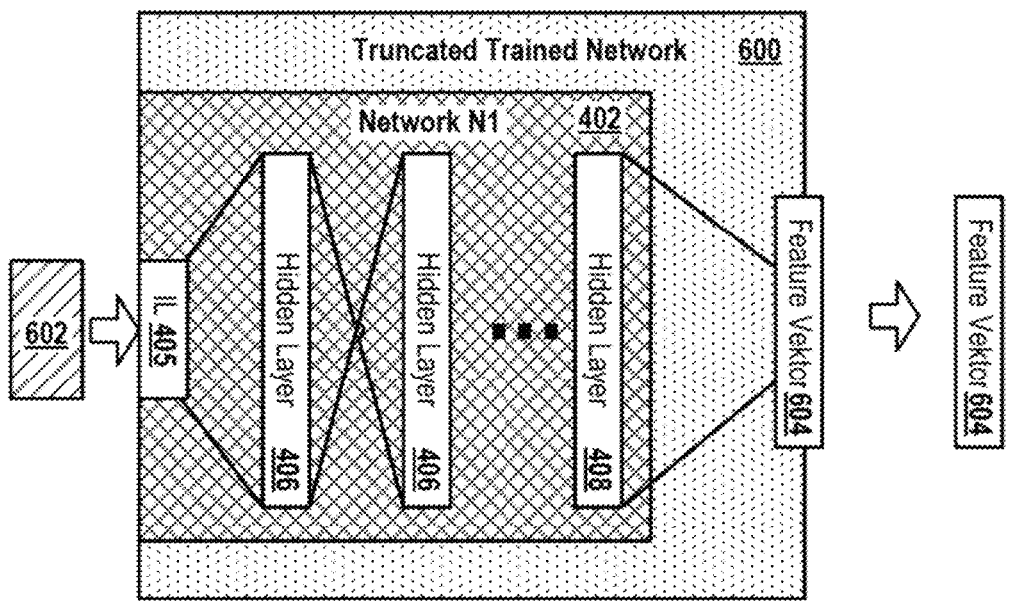
FIG. 6 depicts a vector-output MLM in the form of a truncated Siamese network.

FIG. 6 depicts a vector-output MLM 600 in the form of a truncated Siamese network. The vector-output MLM 600 can be obtained, for example, by storing one of the sub-networks 402, 403 of a trained Siamese network 400' separately. In contrast to the trained Siamese network, the vector-output-MLM requires only a single image 602 as input and does not output a similarity label but rather a feature vector 604 that selectively comprises values of a limited set of features having been identified during the training of the Siamese network 400' as being particularly characteristic for a particular tissue pattern and being particularly suited for determining the similarity of the tissue patterns depicted in two images by extracting and comparing this particular set of features from the two images.

Figure 7:
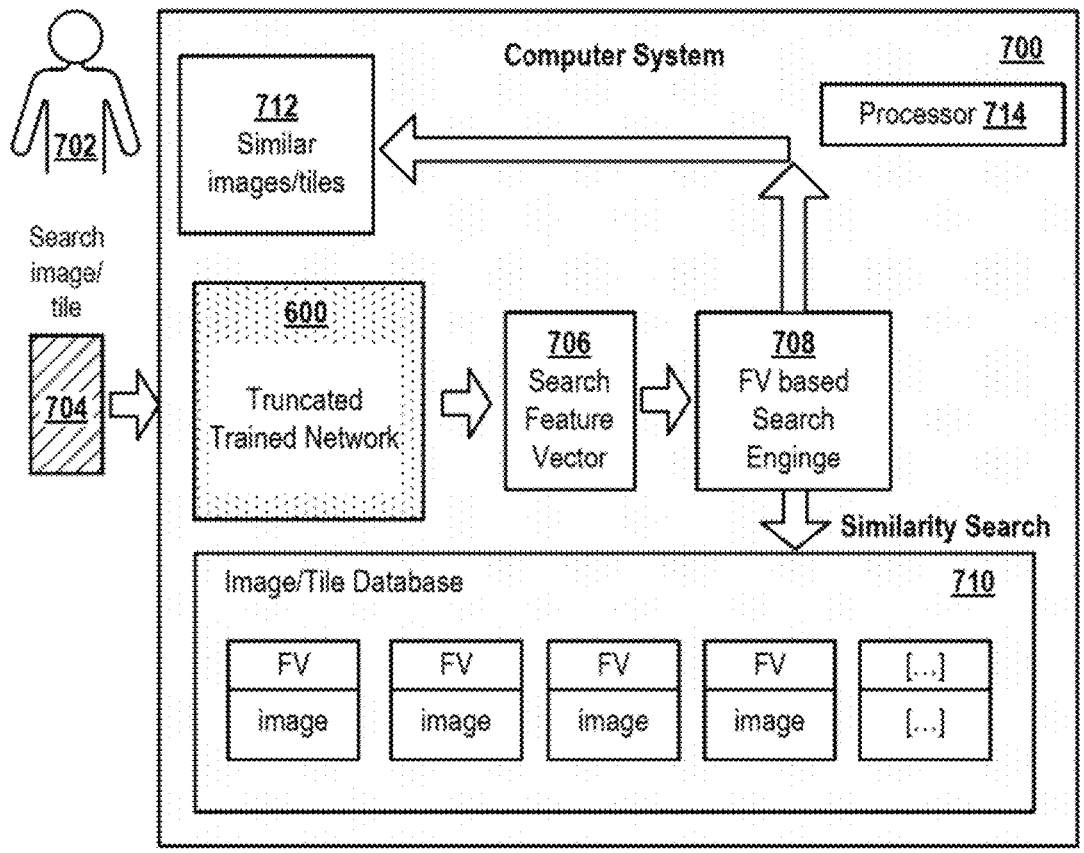
FIG. 7 depicts a computer system using a vector-output MLM for a similarity search in an image database.

FIG. 7 depicts a computer system 700 that comprises one or more processors 714 and a trained vector-output MLM 600 as depicted, for example, in FIG. 6. The system 700 is adapted to perform an image similarity search using the vector-output MLM.

the computer system can be, for example, a standard computer system or a server that comprises or is operatively coupled to a database 710. For example, the database can be a relational BDSM comprising hundreds or even thousands of whole slide images depicting tissue samples of a plurality of patients. Preferably, the database comprises, for each of the images in the database, a respective feature vector that has been extracted by a feature output MLM 600 from the said image in the database. Preferably, the computation of the feature vector of each image in the database is performed in a single, pre-processing step before any such request is received. However, it is also possible to compute and extract the feature vectors for the images in the database dynamically in response to a search request.

The computer system comprises a user interface that enables a user 702 to select or provide a particular image or image tile that is to be used as search image 704. The trained vector-output MLM 600 is adapted to extract a feature vector 706 ("search feature vector") from the input image. a search engine 708 receives the search feature vector 706 from the feature output MLM 600 and performs a vector-based similarity search in the image database. The similarity search comprises comparing the search feature vector which each of the feature vectors of the images in the database in order to compute a similarity score as a function of the two compared feature vectors. The similarity score is indicative of the degree of similarity of the search feature vector with the feature vector of the image in the database and hence indicates the similarity of the tissue patterns depicted in the two compared images. The search engine 708 is adapted to return and output a search result 712 to the user. The search result can be, for example, one or more images of the database for which the highest similarity score was computed.

For example, if the search image 704 is an image tile known to depict breast cancer tissue, the system depicted in FIG. 7 can be used for identifying a plurality of other tiles (or whole slide images comprising such tiles) which depict a similar breast cancer tissue pattern.

The system 700 is an example for an application scenario where the input/output structure of a vector-output-MLM is more appropriate than the input/output structure of a Siamese network.

Figure 8:
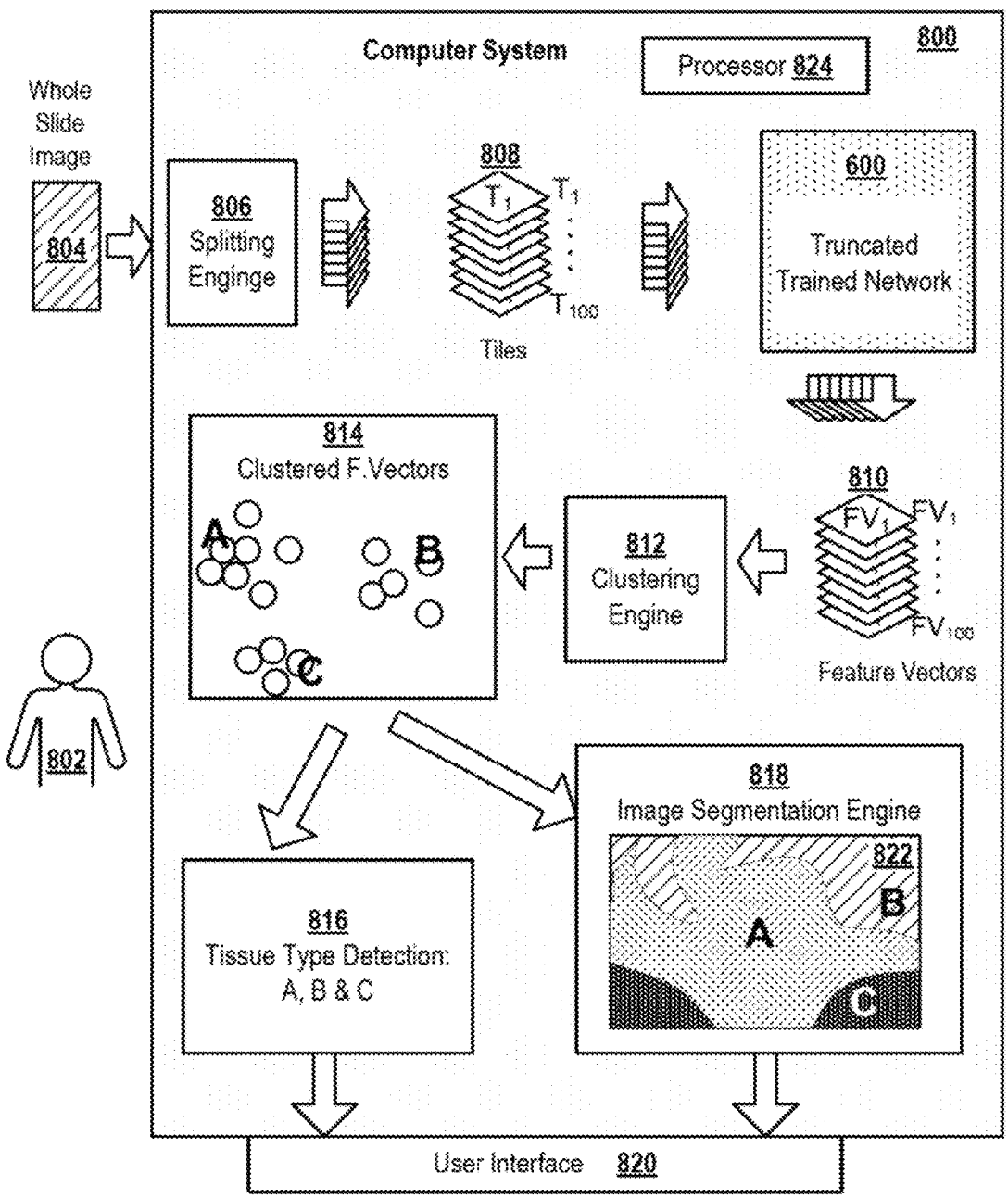
FIG. 8 depicts a computer system using a vector-output MLM for image segmentation and/or cluster analysis.

FIG. 8 depicts a computer system 800 comprising one or more processors 824 and a trained vector-output MLM 600. The system 800 is adapted for performing digital pathology tasks such as image segmentation and/or cluster analysis.

The system comprises an image splitting engine 806 that is adapted to receive an input image, e.g. a whole slide image 804, and generate a plurality of image tiles 808 from the input image. In the depicted example, the tile index ranges from 1 to 100. In fact, the number of tiles generated from the whole slide image is typically much larger, e.g. in the range of multiple thousand or 10,000 tiles.

A trained vector output MLM 600 receives the generated tiles 808 and extracts, from each of the tiles, a respective feature vector. The plurality 810 of the directors computed by the trained MLM 600 is fed into a clustering engine 812. The clustering engine is adapted to perform a clustering of the received feature vectors, e.g. a K-means clustering. As a result of the clustering, a plurality of clusters (groups) 814 of similar feature vectors is automatically identified. in the example depicted in FIG. 8, three similar clusters (A, B and C) of feature vectors have been identified and can be used as a basis for further processing steps. For example, an image segmentation engine 818 can use the clusters 814 for identifying tiles in the received image 804 belonging to the same cluster of feature vectors. All tiles belonging to the same cluster can be identified as image segments as depicted in a segmentation result image 822 where different image segments are indicated using different colors and/or hatchlings. In addition, or alternatively, the identified clusters 814 of feature vectors can be used as a basis for identifying different types of tissue patterns in the input image. For example, a similarity search can be performed for one or more feature vectors of each cluster A, B or C for identifying similar images showing a known tissue types such as "tumor tissue", "slight background", "healthy stroma tissue". The tissue type assigned to the most similar database image identified in the similarity search is considered as the tissue pattern represented by the respective cluster. Thereby, a system and method for automatically identifying different types of tissue patterns in an input image is provided that does not need the creation of a large amount of manually annotated training data.

The splitting engine, the clustering engine and the image segmentation engine can respectively be implemented, for example, as a standalone software application. Alternatively, one or more of the engines 806, 814 and/or 818 can be implemented as sub-modules or program routines of a single, integrated software application.

The system 800 is a further example for application scenarios where the input/output structure of a vector-output-MLM is more appropriate than the input/output structure of a Siamese network.

Figure 9:
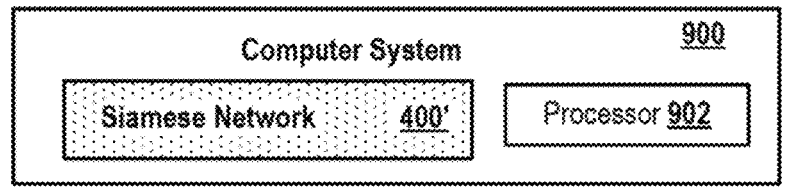
FIG. 9 depicts a computer system using the trained Siamese network for determining the similarity of tissue patterns of two images.

FIG. 9 depicts a computer system 900 comprising one or more processors 902 and a trained Siamese network 400' for determining the similarity of tissue patterns of two images. For example, the Siamese network can be used in all application scenarios where two images or tiles are provided as input and where the similarity of the tissue patterns depicted therein shall be determined quickly.

Figure 10:
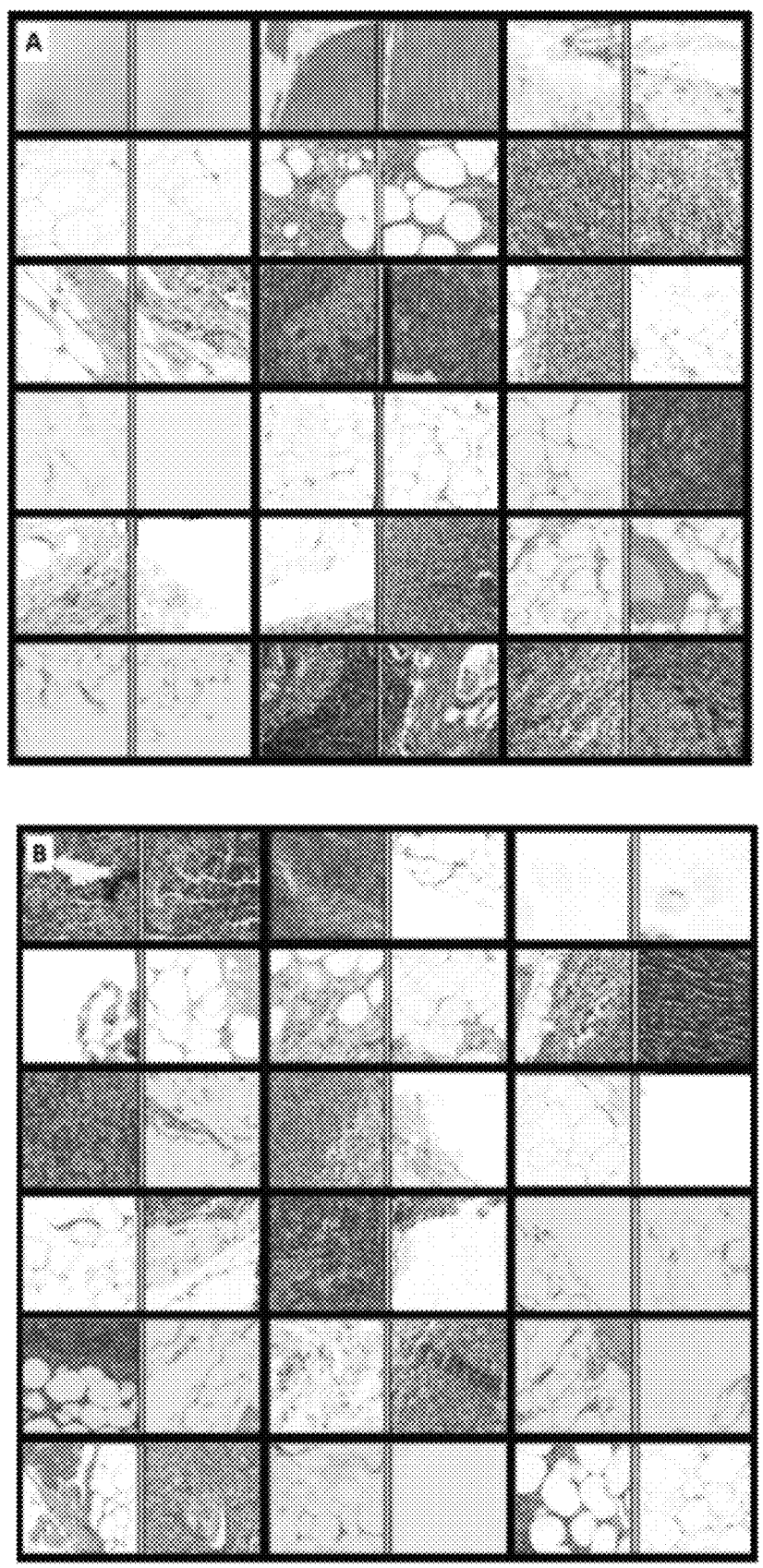
FIG. 10 shows "similar" and "dissimilar" tile pairs labeled based on their spatial proximity.

FIG. 10 shows two tile matrices, each matrix consisting of three columns, each column comprising six tile pairs. The first matrix shows a first set of tile pairs (A) consisting of tiles that lie close to each other and that are automatically assigned the label "similar" tile pair. The second matrix shows a second set of tile pairs (B) lying far from each other and that are automatically assigned the label "dissimilar" tile pair. In some cases "similar" labeled tiles look dissimilar and "not similar" labeled tiles look similar. This noise is caused by the fact that at the border where two different tissue patterns meet, two nearby tiles may depict different tissue patterns and by the fact that even distant tissue regions may depict the same tissue pattern. This is an expected, inherent noise in the dataset generation process.

Applicant has observed that despite of this noise, the predictions of a MLM trained on the automatically labeled data set is highly accurate. Applicant assumes that that the observed robustness of the trained MLMs against this noise is based on the fact that region borders typically have less area than the region non-border areas.

According to embodiments, the quality of the automatically generated training data set is using, in a first step, a previously trained similarity network or an ImageNet pre-trained network to assess similarity of tile pairs, then a second step generate the similarity labels based on the spatial proximity of tiles as described herein for embodiments of the invention and then correct the pair labels where a strong deviation of the similarity of the two tiles determined in the first step on the one hand and in the second step in on the other hand is observed.

Figure 11:
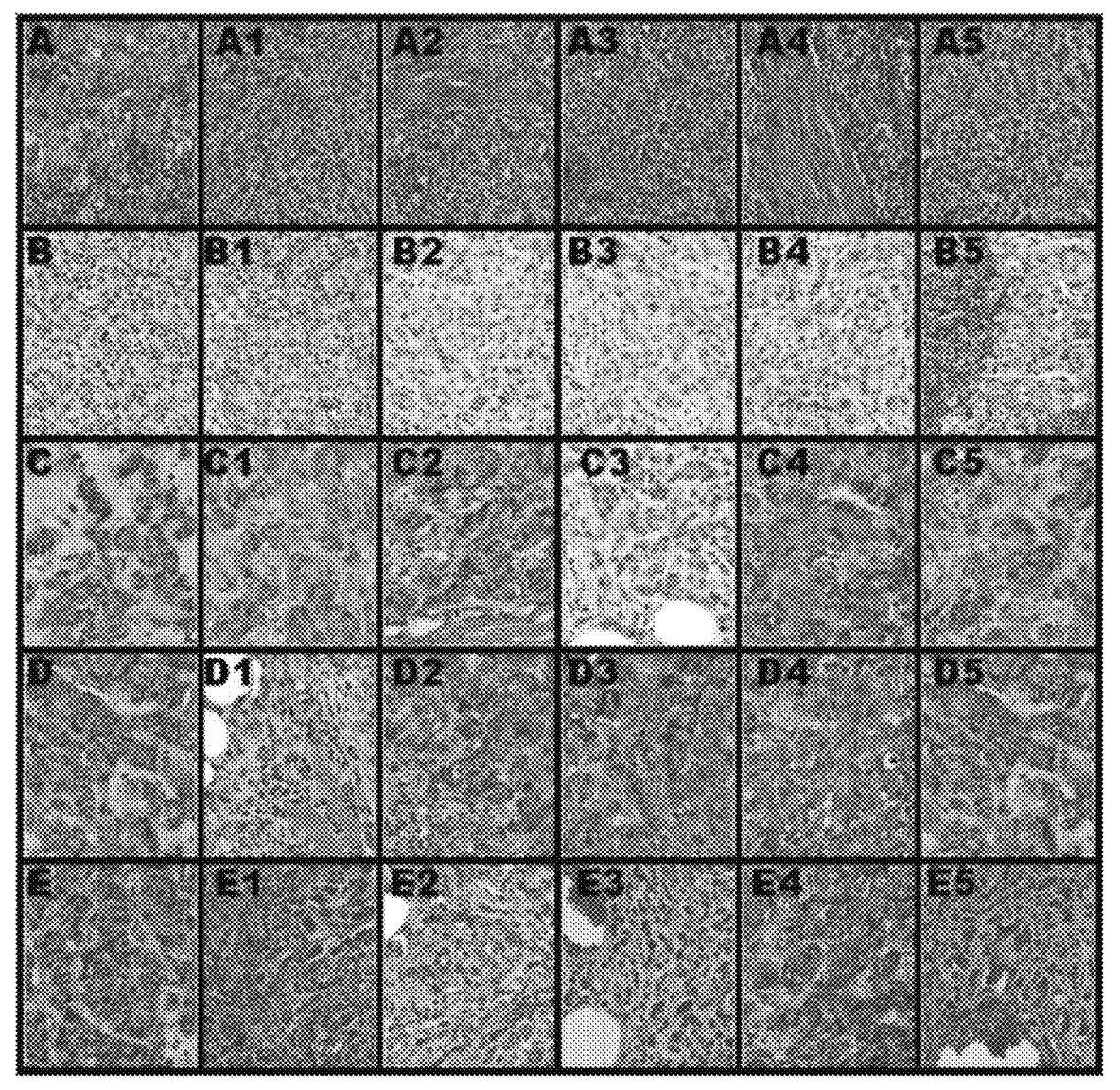

FIG. 11 shows similarity search results for 5 tumor query tiles (A, B, C, D, E) in the image retrieval task and the 5 closest retrieved tiles from slides other than the query slide (A1-A5, B1-B5, C1-C5, D1-D5, E1-E5), ranked by distance from low to high, using feature vectors extracted by a feature-output MLM trained on an automatically labeled data set as described herein for embodiments of the invention. The target class (e.g. tumor) comprises only 3% of the tiles searched. Even though some retrieved tiles look very different than the query tile (e.g. C3 and C) all of the retrieved tiles except A4 have been verified by an expert pathologist to contain tumor cells (i.e. correct class retrieval).

LIST OF REFERENCE NUMERALS

100 method
102-108 steps
202-203 tissue samples of different patients
208-212 tissue samples within a stack of adjacent tissue samples
214-218 tissue samples within a further stack of adjacent tissue samples
220-236 digital images respectively depicting a tissue sample
300 digital tissue image sliced into a plurality of tiles
302 tile T1
304 tile T2
306 tile T3
308 first spatial proximity threshold (2D)
310 second spatial proximity threshold (2D)
312 pair of tiles labeled "similar"
313 pair of tiles labeled "similar"
314 pair of tiles labeled "dissimilar"
315 pair of tiles labeled "dissimilar"
316 training data
332 digital tissue image aligned to image 300
334 digital tissue image aligned to image 332
336 first spatial proximity threshold (3D)
338 second spatial proximity threshold (3D)
340 tile T4
342 tile T5
400 (untrained) Siamese network
400' (trained) Siamese network
402 sub-network
403 sub-network
404 first input tile
405 input layer of first network N1
406 hidden layers
407 proximity-based ("measured") similarity label
408 hidden layer adapted to compute a feature vector for the first input tile
410 feature vector extracted from the first input tile 404
414 second input tile
415 input layer of second network N2
416 hidden layers
418 hidden layer adapted to compute a feature vector for the second input tile
420 feature vector extracted from the second input tile 414
422 pair of input tiles
424 output layer joining networks N1, N2
426 predicted similarity label
428 individual data record of training data set
502 input tile 504 first input tile
506 second input tile
508 predicted similarity label
510 complete data record comprising input tile pair 502 and predicted similarity label 508
600 vector-output MLM
602 individual input image/tile
604 feature vector
700 computer system
702 user
704 individual input image/tile
706 search feature vector
708 feature vector-based search engine
710 database comprising a plurality of images or tiles
712 returned similarity search results
714 processor
800 computer system
802 user
804 individual input image/tile
806 image splitting engine
808 plurality of tiles
810 plurality of feature vectors
812 clustering engine
814 identified clusters of similar feature vectors
816 cluster analysis result: identified tissue types
818 image segmentation engine
820 user interface
822 segmented image
824 processor
900 computer system
902 processor

The invention claimed is:

1. A computer-implemented self-supervised learning method for digital pathology, comprising:
Receiving a plurality of digital images each depicting a tissue sample;
Splitting each of the received images into a plurality of tiles;
automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity, wherein at least a subset of the tile pairs comprise tile pairs depicting two tissue regions contained in two different tissue slices of a stack of adjacent tissue slices, each of the tissue slices being the tissue sample depicted in a respective one of the received digital images, wherein the received images depicting tissue slices of a stack of adjacent tissue slices are aligned with each other in a 3D coordinate system and wherein the distance between the tiles of the tile pairs of the subset is computed within the 3D coordinate system;
training a machine learning module—MLM—using the labeled tile pairs as training data to generate a trained MLM, the trained MLM being configured for performing an image analysis of digital histopathology images,
wherein at least a further subset of the tile pairs comprise tile pairs depicting two tissue regions of the same tissue slice, wherein the distance between the tiles of the tile pairs of the further subset is computed based on the same function of the spatial proximity as the distance between the tile pairs of the subset of tile pairs derived depicting different tissue slice.

2. The computer-implemented method of claim 1, where each of the tissue slices is depicted in a respective one of the received digital images, wherein the distance between tiles of the further subset of the tile pairs is computed within a 2D coordinate system defined by the x- and y-dimension of the received digital image from which the tiles in the pair have been derived.

3. The computer-implemented method of claim 1, each tile depicting a tissue or background region having a maximum edge length of less than 0.5 mm, preferably less than 0.3 mm.

4. The computer-implemented method of claim 1, the automatic generation of the tile pairs comprising:
generating a first set of tile pairs using a first spatial proximity threshold, wherein the two tissue regions depicted by the two tiles of each tile pair in the first set are separated from each other by a distance smaller than the first spatial proximity threshold;
generating a second set of tile pairs using a second spatial proximity threshold, wherein the two tissue regions depicted by the two tiles of each tile pair in the second set are separated from each other by a distance larger than the second spatial proximity threshold.

5. The computer-implemented method of claim 4, the second spatial proximity threshold being at least 2 mm larger than the first spatial proximity threshold.

6. The computer-implemented method of claim 4, wherein the first spatial proximity threshold is a distance smaller than 2 mm, preferably smaller than 1.5 mm, in particular 1.0 mm, and/or wherein the second spatial proximity threshold is a distance larger than 4 mm, preferably larger than 8 mm, in particular 10.0 mm.

7. The computer-implemented method of claim 1, wherein the MLM is a Siamese neuronal network comprising two identical neuronal sub-networks joined by a common output layer, each of the two neural sub-networks being configured to extract a feature-vector from a respective one of the two tiles of a tile pair provided as input to the MLM,
wherein the output layer of the trained Siamese neuronal network is configured to compute a label for each tile pair provided as input as a function of the two feature vectors, the label being indicative of a predicted similarity of the two tissue patterns depicted in the tile pair provided as input.

8. The computer-implemented method of claim 7, wherein the MLM is the Siamese network, the method further comprising providing the vector-output MLM, the providing of the vector-output-MLM comprising:
storing one of the sub-networks of the trained Siamese network separately on a storage medium; and
using the stored sub-network as the vector-output MLM.

9. The computer-implemented method according to claim 1,
wherein the MLM is or comprises a vector-output MLM, the vector-output MLM being a MLM that is configured to receive a single digital image or tile as input and that is configured to output a feature vector extracted from said image or tile,
whereby the training of the MLM on the labeled tile pairs comprises a backpropagation operation and wherein during backpropagation a predictive model of the MLM is changed such that the features in the vector extracted by the MLM comprises features that are characteristic for a particular tissue pattern and that enable a vector-comparison based identification of similar and dissimilar image pairs.

10. The computer-implemented method according to claim 9, further comprising:
- Providing a digital search image as input of the vector-output-MLM, the search image depicting a tissue sample or a sub-region thereof;
- Extracting, by the vector-output-MLM, a search feature vector from the search image;
- Performing, by a similarity search engine, a similarity search in an image database of digital tissue sample images, the similarity search engine determining the similarity of the search feature vector with feature vectors extracted by the vector-output-MLM for each of the images in the image database; and
- Returning the ones of the images in the database whose feature vectors are the most similar to the search feature vector as a result of the similarity search.

11. The computer-implemented method according to claim 9, further comprising:
- Providing a digital image as input of the vector-output-MLM, the digital image depicting a whole slide tissue sample or a sub-region thereof;
- Splitting the provided digital image into a plurality of tiles;
- Extracting, by the vector-output-MLM, a feature vector from each of the tiles;
- Clustering, by a clustering engine, the feature vectors extracted from the plurality of tiles, thereby creating clusters of similar feature vectors;
- Grouping the plurality of tiles into clusters of tiles in accordance with the clusters computed for the tiles' feature vectors; and
- Outputting, via a graphical user interface, the clusters of tiles.

12. The computer-implemented method according to claim 11, further comprising:
- Identifying segments in the provided digital image, wherein each segment is a group of adjacent tiles and wherein all tiles within each segment belong to the same one of the identified clusters of tiles; and
- Outputting, via the graphical user interface, an optical indication of the identified segments in the provided digital image.

13. The computer-implemented method according to claim 9, further comprising:
- Providing a digital search image as input of the vector-output-MLM, the search image depicting a tissue sample or a sub-region thereof;
- Extracting, by the vector-output-MLM, a search feature vector from the search image;
- Performing, by a similarity search engine, a similarity search in an image database of digital tissue sample images, the similarity search engine determining the similarity of the search feature vector with feature vectors extracted by the vector-output-MLM for each of the images in the image database; and
- Returning the ones of the images in the database whose feature vectors are the most similar to the search feature vector as a result of the similarity search.

14. A non-volatile storage medium comprising computer-interpretable instructions which, when executed by a processor, instantiate and/or execute a trained machine learning module—MLM—generated by a computer-implemented method according to claim 1.

15. An image analysis system comprising:
- at least one processor;
- a volatile or non-volatile storage medium, the storage medium comprising a trained a trained machine learning module—MLM—generated by a computer-implemented method according to claim 1.

16. A computer-implemented self-supervised learning method for digital pathology, comprising:
- Receiving a plurality of digital images each depicting a tissue sample;
- Splitting each of the received images into a plurality of tiles;
- automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity, wherein at least a subset of the tile pairs comprise tile pairs depicting two tissue regions contained in two different tissue slices of a stack of adjacent tissue slices, each of the tissue slices being the tissue sample depicted in a respective one of the received digital images, wherein the received images depicting tissue slices of a stack of adjacent tissue slices are aligned with each other in a 3D coordinate system and wherein the distance between the tiles of the tile pairs of the subset is computed within the 3D coordinate system;
- training a machine learning module—MLM—using the labeled tile pairs as training data to generate a trained MLM, the trained MLM being configured for performing an image analysis of digital histopathology images, wherein the automatic generation of the tile pairs includes
  - generating a first set of tile pairs using a first spatial proximity threshold, wherein the two tissue regions depicted by the two tiles of each tile pair in the first set are separated from each other by a distance smaller than the first spatial proximity threshold, and
  - generating a second set of tile pairs using a second spatial proximity threshold, wherein the two tissue regions depicted by the two tiles of each tile pair in the second set are separated from each other by a distance larger than the second spatial proximity threshold.

17. The computer-implemented method of claim 16, the second spatial proximity threshold being at least 2 mm larger than the first spatial proximity threshold.

18. The computer-implemented method of claim 16,
- wherein the first spatial proximity threshold is a distance smaller than 2 mm, preferably smaller than 1.5 mm, in particular 1.0 mm, and/or
- wherein the second spatial proximity threshold is a distance larger than 4 mm, preferably larger than 8 mm, in particular 10.0 mm.

19. A computer-implemented self-supervised learning method for digital pathology, comprising:
- Receiving a plurality of digital images each depicting a tissue sample;
- Splitting each of the received images into a plurality of tiles;
- automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity, wherein at least a subset of the tile pairs comprise tile pairs depicting two tissue regions contained in two different tissue slices of a stack of adjacent tissue slices, each of the tissue slices being the tissue sample depicted in a respective one of the received digital images, wherein the received images depicting tissue slices of a stack of adjacent tissue slices are aligned with each other in a 3D coordinate system and wherein the distance between the tiles of the tile pairs of the subset is computed within the 3D coordinate system;

training a machine learning module—MLM—using the labeled tile pairs as training data to generate a trained MLM, the trained MLM being configured for performing an image analysis of digital histopathology images, wherein the MLM is or comprises a vector-output MLM, the vector-output MLM being a MLM that is configured to receive a single digital image or tile as input and that is configured to output a feature vector extracted from said image or tile, whereby the training of the MLM on the labeled tile pairs comprises a backpropagation operation and wherein during backpropagation a predictive model of the MLM is changed such that the features in the vector extracted by the MLM comprises features that are characteristic for a particular tissue pattern and that enable a vector-comparison based identification of similar and dissimilar image pairs.

* * * * *